(12) United States Patent
Poenie et al.

(10) Patent No.: US 8,921,088 B1
(45) Date of Patent: Dec. 30, 2014

(54) REVERSIBLY BINDING RESIN FOR ALGAL HARVEST AND CONCENTRATION

(71) Applicant: Board of Regents, The University of Texas System, Austin, TX (US)

(72) Inventors: Martin Poenie, Austin, TX (US); Jessica Jones, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 32 days.

(21) Appl. No.: 13/644,050

(22) Filed: Oct. 3, 2012

Related U.S. Application Data

(60) Provisional application No. 61/542,662, filed on Oct. 3, 2011.

(51) Int. Cl.
*C12N 1/00* (2006.01)
(52) U.S. Cl.
USPC ........ 435/243; 435/257.1; 435/946; 210/683; 203/33; 204/539; 205/517
(58) Field of Classification Search
CPC ...... C12P 7/6463; C12P 7/649; C12P 7/6409; C12P 7/64; C12P 5/02; C12P 7/20; C12P 7/6418; C12P 7/6436; C12P 33/00; C12P 7/16; C12P 7/6472; C12P 7/10; C12P 13/04; C12P 13/08; C12P 17/04; C12P 7/02; C12P 7/06; C12P 7/065
USPC ........ 435/243, 257.1, 946; 204/539; 205/517; 203/33; 210/683
See application file for complete search history.

(56) References Cited

U.S. PATENT DOCUMENTS

| | | | | |
|---|---|---|---|---|
| 4,882,275 | A * | 11/1989 | Klagsbrun | 435/70.3 |
| 6,805,800 | B1 | 10/2004 | Keating | |
| 8,329,449 | B2 | 12/2012 | Poenie et al. | |
| 2012/0289692 | A1 * | 11/2012 | Gray et al. | 536/56 |

OTHER PUBLICATIONS

Ayoub, et al. "Seawater induced algal flocculation, Water Research", vol. 20, No. 10, pp. 1265-1271 (1986).
Banerjee, et al. "*Botryococcus braunii*: A Renewable Source of Hydrocarbons and Other Chemicals", Critical Reviews in Biotechnology, 22(3):245-279 (2002).
Bosma, et al. "Ultrasound, a new separation technique to harvest microalgae", Journal of Applied Phycology 15:143-153 (2003).
Christy, Yusuf "Biodiesel from microalgae", Biotechnology Advances 25 (2007), 294-306.
Dziubek, et al. "Effect of magnesium hydroxide on chemical treatment of secondary effluent under alkaline conditions", Proceedings of the Water Reuse Symposium III (pp. 1428-1436), San Diego: AWWA Research Foundation (1984).
Dziubek, et al. "High-pH coagulation-adsorption: A new technology for water treatment and reuse", Water Science and Technology, vol. 21,Brighton, pp. 511-517 (1989).
Elmaleh, et al. Suspended solids abatement by pH increase—Upgrading of an oxidantion pond effluent, Water Research, vol. 30, No. 10, pp. 2357-2362, (1996).
Folkman, et al. "Removal of algae from stabilization pond effluents by lime treatment", Water Research, Pergamon Press 1973, vol. 7, pp. 419-435.
Gavrilescu, et al. "Biotechnology—A sustainable alternative for chemical industry", Biotechnology Advances 23, pp. 471-449, (2005).
Grima, et al. "Recovery of microalgal biomass and metabolites: Process options and economics", Biotechnology Advances 20, pp. 491-515, (2003).
Harwood, et al. "The versatility of algae and their lipid metabolism", Biochimie 91,679-684, (2009).
Hung, et al. "Microfiltration for separation of green algae from water", Colloids and Surfaces B: Biointerfaces 51 (2006), 157-164.
Jones, et al. Extraction of Algal Lipids and Their Analysis by HPLC and Mass Spectrometry, Journal of the American Oil Chemists' Society (2012), 89:1371-1381.
Kara, et al. "Poly (ethylene glycol dimethacrylate—n-vinyl imidazole) beads for heavy metal removal", Journal of Hazardous Materials 106B (2004), pp. 93-99.
Lavoie, et al. "Harvesting of *Scenedesmus obliquus* in Wastewaters: Auto- or bioflocculation?" Biotechnology and Bioengineering, vol. 30, pp. 852-859 (1987).
Li, et al. "Biofuels from Microalgae", Biotechnology Progress (2008) 24, pp. 815-820.
Li, et al. "Perspectives of microbial oils for biodiesel production", Applied Microbiology and Biotechnology 80:749-756 (2008).
Munoz, et al. "Algal-bacterial processes for the treatment of hazardous contaminants: A review", Water Research 40, pp. 2799-2815 (2006).
Olaizola, Miguel "Commercial development of microalgal biotechnology: from the test tube to the marketplace", Biomolecular Engineering 20 (2003), pp. 459-466.
Park, et al. "Recycling algae to improve species control and harvest efficiency from a high rate algal pond", Water Research 45, pp. 6637-6649 (2011).
Pyle, et al. "Producing Docosahexaenoic Acid (DHA)-Rich Algae from Biodiesel-Derived Crude Glycerol: Effects of Impurities on DHA Production and Algal Biomass Composition", Journal of Agricultural and Food Chemistry 56, pp. 3933-3939 (2008).

(Continued)

*Primary Examiner* — Susan Hanley
*Assistant Examiner* — Nghi Nguyen
(74) *Attorney, Agent, or Firm* — Edwin S. Flores; Daniel J. Chalker; Chalker Flores, LLP

(57) ABSTRACT

The present invention includes a method for harvesting or separating one or more biological cells from an aqueous feed, a stream, a suspension, or any combinations thereof by providing the aqueous feed, the stream, or the suspension comprising the one or more biological cells in a tank or a vessel; providing one or more ion-exchange resins, wherein the ion-exchange resin is an anion-exchange resin; contacting the anion-exchange resin with the aqueous feed; binding the one or more biological cells to the anion-exchange resin; releasing or eluting the bound one or more biological cells by changing the pH; and collecting the released one or more biological cells to obtain a concentrated slurry or suspension of the one or more biological cells.

41 Claims, 7 Drawing Sheets

(56) References Cited

OTHER PUBLICATIONS

Schlesinger, et al. "Inexpensive non-toxic flocculation of microalgae contradicts theories: overcoming a major hurdle to bulk algal production", Biotechnology Advances 30 (2012) 1023-1030.

Shelef, et al. "Microalgae Harvesting and Processing: A Literature Review" A subcontract Report, Springfield: National Technical Information Service, Aug. 1984.

Shin, et al. "Removal of Nutrients in Wastewater by using Magnesium Salts", Environmental Technology, vol. 19, pp. 283-290 (1997).

Uduman, et al. "Dewatering of micralgal cultures: A major bottleneck to algae-based fuels", Journal of Renewable and Sustainable Energy 2, 012701, (2010). pp. 1-15.

Wiley, et al. "Improved Algal Harvesting Using Suspended Air Flotation", Water Environment Research, vol. 81, No. 7, pp. 702-708, Jul. 2009.

Yahi, et al. "Algal flocculation-sedimentation by pH increase in a continuous reactor", Water Science and Technology, vol. 30, No. 8, pp. 259-267 (1994).

\* cited by examiner

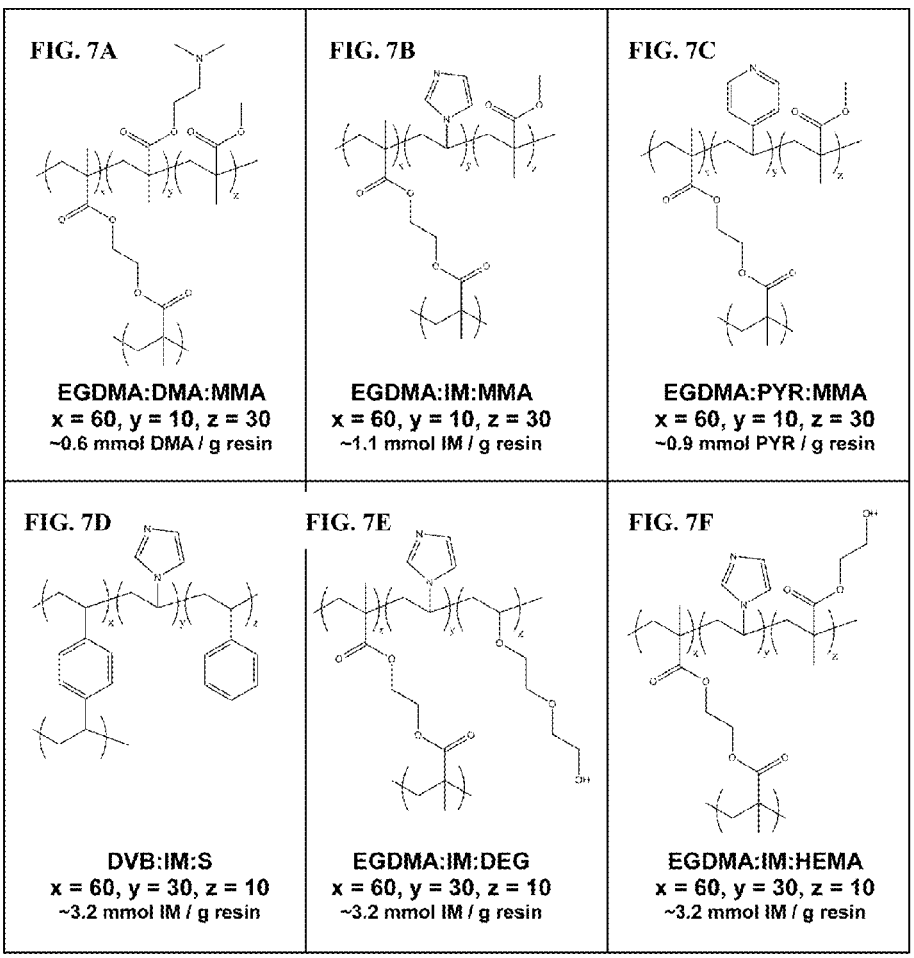

REVERSIBLY BINDING RESIN FOR ALGAL HARVEST AND CONCENTRATION

CROSS-REFERENCE TO RELATED APPLICATIONS

This application claims priority to U.S. Provisional Application Ser. No. 61/542,662, Filed Oct. 3, 2011, the entire contents of which are incorporated herein by reference.

TECHNICAL FIELD OF THE INVENTION

The present invention relates in general to the field of processing biomasses to yield commercially valuable products, and more particularly, to the development and use of resins that reversibly bind algae as a function of the pH for the purposes of dewatering and concentration of the algae.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with column and resin based methods for algal processing.

U.S. Patent Application Publication No. 2011/0083360 (Poenie et al. 2011) discloses a reverse phase extraction method for the recovery of triglycerides from aqueous slurries of algae is described herein. The present invention discloses the use of immobilized anion exchange and lipid binding resins. As the algae flows past the resin, triglycerides adhere while the bulk of the algae flows through. The lipids, useful for generating biofuels are then are eluted off the resin. The method of the present invention does not require prior drying of the algae, is inexpensive, and does not destroy the algal biomass which can be used for other purposes.

U.S. Pat. No. 6,805,800 issued to Keating (2004) describes a method of recovering fat soluble compounds, including but not restricted to pigments such as beta-carotene, from solutions, including but not restricted to those solutions containing microalgal cells. According to the Keating patent, the method comprises passing a solution containing a fat soluble compound is passed through a fluidized bed of crystalline metallic ore particles, such as magnetite, allowing the fat soluble compound to bind to the particles to form a complex. The fat soluble compound is released from the complex by passing a wash solution through the fluidized bed and is subsequently collected in the solution.

SUMMARY OF THE INVENTION

The present invention describes a resin-based method for harvesting and concentrating algae from suspensions. weak anion-exchange resins of the present invention are capable of binding and releasing algae as a function of the pH. The method of the present invention can be used to harvest algae using known mechanical methods and is an improvement over other methods (e.g., flocculation, bulk flocculation, or pond flocculation) in that it is reversible, nontoxic, and that the binding substrate is recoverable and reusable.

In one embodiment the instant invention discloses a method for harvesting or separating one or more biological cells from an aqueous feed, a stream, a suspension, or any combinations thereof comprising the steps of: (i) providing the aqueous feed, the stream, or the suspension comprising the one or more biological cells in a tank or a vessel; (ii) providing one or more ion-exchange resins, wherein the ion-exchange resin is a weak anion-exchange resin (e.g., based on various weak bases), wherein the anion-exchange resin may be packed in a column, attached to a substrate, be in a solution, or any combinations thereof; (iii) contacting the anion-exchange resin with the aqueous feed, the stream, or the suspension comprising the one or more biological cells; (iv) binding the one or more biological cells to the anion-exchange resin, wherein the binding is done by maintaining a specific pH; (v) releasing or eluting the bound one or more biological cells by changing the pH by addition of an acid, a base, or one or more chemicals, wherein the change in the pH involves an increase or a decrease in the pH; and (vi) collecting the released one or more biological cells to obtain a concentrated slurry or suspension of the one or more biological cells.

In one aspect of the method disclosed hereinabove the one or more biological cells comprise algal cells, bacterial cells, viral particles, or combinations thereof. In another aspect the one or more algal cells comprise microalgae selected from a class comprising Bacillariophyceae, Eustigmatophyceae, and Chrysophyceae. In yet another aspect the microalgal genera are selected from the group consisting of *Nannochloropsis, Chlorella, Dunaliella, Scenedesmus, Selenastrum, Oscillatoria, Phormidium, Spirulina, Amphora,* and *Ochromonas.*

In a related aspect the microalgal species are selected from the group consisting of *Achnanthes orientalis, Agmenellum* spp., *Amphiprora hyaline, Amphoracoffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorellakessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlo-*

*rella vulgaris, Chlorococcum infusionum, Chlorococcum sp., Chlorogonium, Chroomonas sp., Chrysosphaera sp., Cricosphaera sp., Crypthecodinium cohnii, Cryptomonas sp., Cyclotella cryptica, Cyclotella meneghiniana, Cyclotella sp., Dunaliella sp., Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera sp., Effipsoidon sp., Euglena spp., Franceia sp., Fragilaria crotonensis, Fragilaria sp., Gleocapsa sp., Gloeothamnion sp., Haematococcus pluvialis, Hymenomonas sp., lsochrysis aff. galbana, lsochrysis galbana, Lepocinclis, Micractinium, Micractinium, Monoraphidium minutum, Monoraphidium sp., Nannochloris sp., Nannochloropsissalina, Nannochloropsis sp., Navicula acceptata, Navicula biskanterae, Navicula pseudotenelloides, Navicula pelliculosa, Navicula saprophila, Navicula sp., Nephrochloris sp., Nephroselmis sp., Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia sp., Ochromonas sp., Oocystis parva, Oocystis pusilla, Oocystis sp., Oscillatoria limnetica, Oscillatoria sp., Oscillatoria subbrevis, Parachlorella kessleri, Pascheriaacidophila, Pavlova sp., Phaeodactylum tricomutum, Phagus, Phormidium, Platymonas sp., Pleurochrysis camerae, Pleurochrysis dentate, Pleurochrysis sp., Prototheca wickerhamii, Prototheca stagnora, Prototheca portoricensis, Prototheca moriformis, Prototheca zopfii, Pseudochlorella aquatica, Pyramimonas sp., Pyrobotrys, Rhodococcus opacus, Sarcinoid chrysophyte, Scenedesmus armatus, Schizochytrium, Spirogyra, Spirulina platensis, Stichococcus sp., Synechococcus sp., Synechocystisf, Tagetes erecta, Tagetes patula, Tetraedron, Tetraselmis sp., Tetraselmis suecica, Thalassiosira weissflogii,* and *Viridiella fridericiana.*

In a specific aspect the one or more algal cells comprise *Neochloris oleoabundans* or *Chlorella*. In one aspect the anion-exchange resins comprise a cross-linked polymer backbone with one or more functional groups comprising ammonium salts, tertiary amines, secondary amines, primary amines, organometallic complexes, aromatic amines, amidine or guanidine groups, any charged species, or any combinations thereof. In another aspect the polymer backbone is a selected from the group consisting of styrene, styrene-divinyl benzene, polystyrene, formophenolic, acrylic-divinyl benzene, methacryl-divinyl benzene, functionalized styrene monomers, functionalized acrylic monomers, functionalized metharcylic monomers, acrylamides, methacrylamides, epoxy and acrylic monomers, polypropylene, or functionalized polyvinyl chloride polymers. In yet another aspect the one or more functional groups comprise triethylene tetramine, nitrate, piperazine, diethylenetetramine, didisopropyl ethylamine, aniline, dimethylaminoethyl methacrylate (DMA), vinyl 2-imidazole, vinyl 4-imidazole (IM), hydroxyethyl methacrylate (HEMA), di(ethylene glycol) vinyl ether (DEG), or any combinations thereof. In a specific aspect the polymer backbone is a methacrylate or a divinyl benzene and the functional group is selected from the group consisting of DEG, DMA, IM, PYR, or any combinations thereof.

The method as described hereinabove further comprises the steps of: processing the concentrated slurry comprising the one or more biological cells in a processing unit to yield an oil or biodiesel and reusing the anion-exchange resin to harvest or separate a subsequent batch of the one or more biological cells from the aqueous feed, the stream, the suspension, or any combinations thereof. The processing unit described herein can include, e.g., (a) one or more lysing units to electromechanically lyse the one or more biological cells by an application of an electromagnetic field, wherein the lysis results in a release of one or more cellular components comprising oils, neutral lipids, proteins, triglycerides, sugars or combinations and modifications thereof from the biological cells;

(b) one or more separations unit to separate the released oils and lipids from the medium resulting in a generation of a residual biomass; and (c) one or more optional pumping equipment, heat exchangers, distilling equipment, reboilers, condensors, and combinations and modifications thereof.

In one aspect the release or elution of the bound one or more biological cells is accomplished in a pH range of 8-13. In another aspect a pKa value of the one or more anion-exchange resins ranges from 5.5-12. In yet another aspect the method results in a 50-fold or greater concentration of the one or more biological cells. In another aspect, when the eluting base is a calcium hydroxide solution (as prepared by, e.g., hydrating lime or quicklime) or magnesium hydroxide solution, the algae will spontaneously flocculate after elution and upon standing. This provides an alternative method to flocculate algae with particular benefits over current methods. In one aspect, the method further comprises the step of eluting the biological cells in the presence of a base, wherein the biological cells spontaneously flocculate after elution and upon standing. In one aspect, the method further comprises the step of eluting the biological cells in the presence of a base selected from at least one of calcium hydroxide or magnesium hydroxide, and wherein the algae spontaneously flocculate after elution and upon standing and are collected using a plate settler, a filtration system, or a partitioning system. In another aspect, the biological cell flocculation occurs solely in the presence of the resin. In another aspect, the biological cell flocculation occurs in the presence of the resin, however, the biological cells can be separated from the water prior to elution of the biological cells from the resin. In one aspect, the method further comprises the step of eluting the biological cells from the resin in the presence of an alcohol and a base catalyst, wherein fatty acids obtained from the biological cells are directly transesterified by the alcohol leading to direct formation of the corresponding fatty acid ester. In one aspect, the method further comprises the step of eluting the biological cells from the resin in the presence of an alcohol selected from at least one of methanol, ethanol, propanol, butanol, or hexanol, and a base catalyst selected from at least one of sodium methoxide, sodium ethoxide, sodium hydroxide or potassium hydroxide, wherein fatty acids obtained from the biological cells are directly transesterified by the alcohol leading to direct formation of the corresponding fatty acid ester. In one aspect, the method further comprises the step of eluting the biological cells from the resin in the presence of an alcohol selected from at least one of methanol, ethanol, propanol, butanol, or hexanol, in the presence of an acid catalyst (e.g., sulfuric acid, hydrochloric acid, or phosphoric acid) and wherein fatty acids obtained from the biological cells are directly transesterified by the alcohol leading to direct formation of the corresponding fatty acid ester. In another aspect, the anion exchange resin is selected from at least one of:

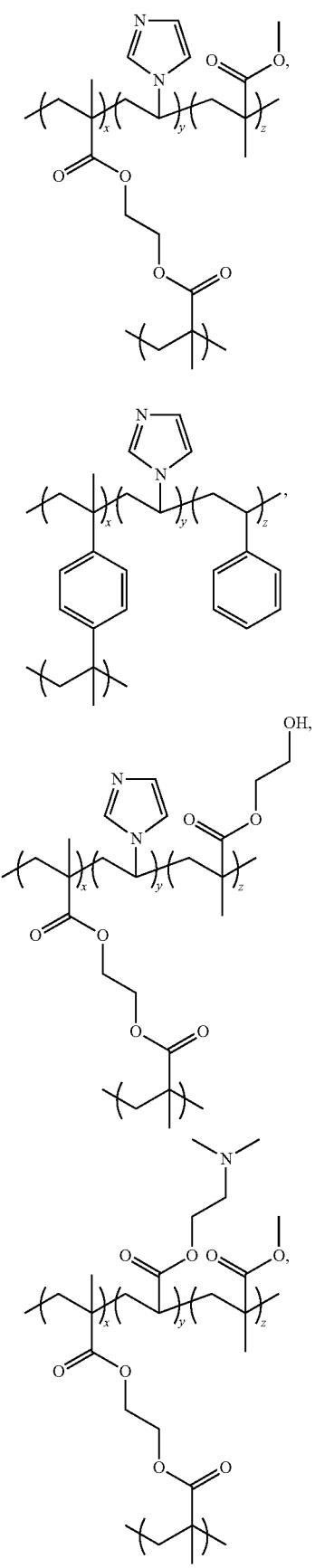

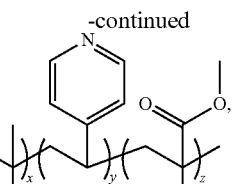
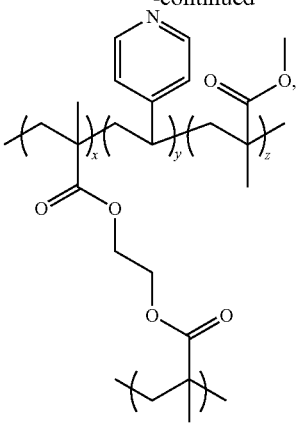
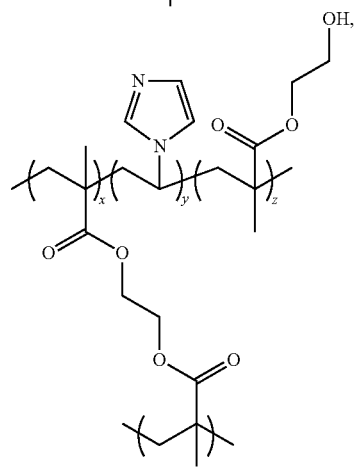

wherein x=60, y is a number ranging from 10-30, and z is a number ranging from 10-30.

Another embodiment of the present invention relates to a method for harvesting or separating one or more algal cells from an aqueous feed, slurry, or suspension comprising the steps of: i) providing the aqueous feed, the slurry, or the suspension comprising the one or more algal cells; ii) saturating an anion-exchange resin in a column or a container with the algal suspension or slurry; iii) binding the one or more algal cells to the anion-exchange resin, wherein the binding is done by maintaining a specific pH; iv) flowing an eluent through the algae saturated column to release or elute the bound algae off the column by a change in the pH, wherein the change in the pH is achieved by addition of an acid, a base, or one or more chemicals; and v) collecting the released one or more algal cells to obtain a concentrated slurry or suspension of the one or more biological cells.

The method as described hereinabove further comprises the optional steps of: a) removing any excess water of liquids from the column or the container by applying a gas pressure, applying a vacuum, or air drying the column, film, coating, or container or using a combination of other drying techniques; b) processing the concentrated slurry comprising the one or more algal cells in a processing unit to yield an oil or biodiesel; and c) reusing the anion-exchange resin to harvest or separate a subsequent batch of the one or more algal cells from the aqueous feed, the slurry, or the suspension. In one aspect the one or more algal cells comprise microalgae selected from a class comprising Bacillariophyceae, Eustigmatophyceae, and Chrysophyceae. In another aspect the microalgal genera are selected from the group consisting of

*Nannochloropsis, Chlorella, Dunaliella, Scenedesmus, Selenastrum, Oscillatoria, Phormidium, Spirulina, Amphora,* and *Ochromonas.* In yet another aspect the microalgal species are selected from the group consisting of *Achnanthes orientalis, Agmenellum* spp., *Amphiprora hyaline, Amphoracoffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorellakessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Effipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis-salina, Nannochloropsis* sp., *Navicula acceptata, Navicula biskanterae, Navicula pseudotenelloides, Navicula pellicu-losa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheriaacidophila, Pavlova* sp., *Phaeodactylum tricomutum, Phagus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana.*

In a specific aspect of the method the one or more algal cells comprise *Neochloris oleoabundans* or *Chlorella.* In one aspect the anion-exchange resins comprise a cross-linked polymer backbone with one or more functional groups comprising ammonium salts, tertiary amines, secondary amines, primary amines, organometallic complexes, aromatic amines, amidine, or guanidine groups, any charged species, or any combinations thereof. In other aspects the polymer backbone is a selected from the group consisting of styrene, styrene-divinyl benzene, polystyrene, formophenolic, acrylic-divinyl benzene, methacryl-divinyl benzene, functionalized styrene monomers, functionalized acrylic monomers, functionalized metharcylic monomers, acrylamides, methacrylamides, epoxy and acrylic monomers, polypropylene, or functionalized polyvinyl chloride polymers and the one or more functional groups comprise triethylene tetramine, nitrate, piperazine, diethylenetetramine, didisopropyl ethylamine, aniline, dimethylaminoethyl methacrylate (DMA), vinyl 2-imidazole, vinyl 4-imidazole (IM), hydroxyethyl methacrylate (HEMA), or any combinations thereof. In another aspect the polymer backbone is a methacrylate or a divinyl benzene and the functional group is selected from the group consisting of DMA, IM, PYR, or any combinations thereof.

In yet another aspect the anion-exchange resin is selected from a group consisting of:

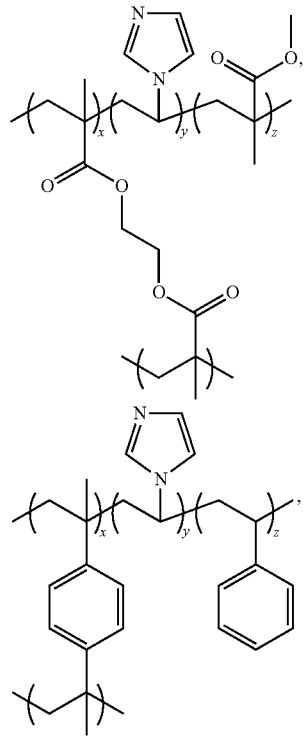

-continued

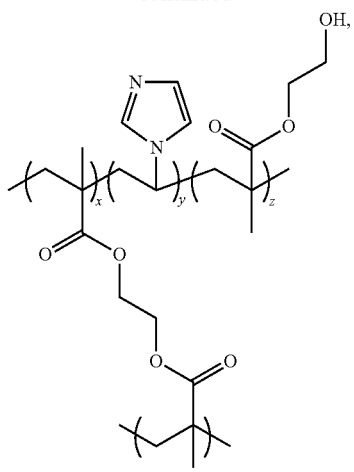

and

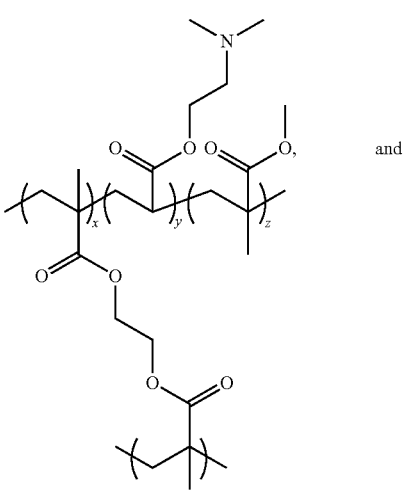

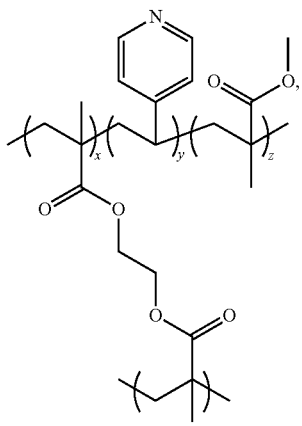

wherein x=60, y is a number ranging from 10-30, and z is a number ranging from 10-30. In one aspect the release or elution of the bound one or more biological cells is accomplished in a pH range of 8-13. In another aspect a pKa value of the one or more anion-exchange resins ranges from 5.5-12. In yet another aspect the method results in a 50-70 fold concentration of the one or more biological cells.

In another aspect the resin comprises

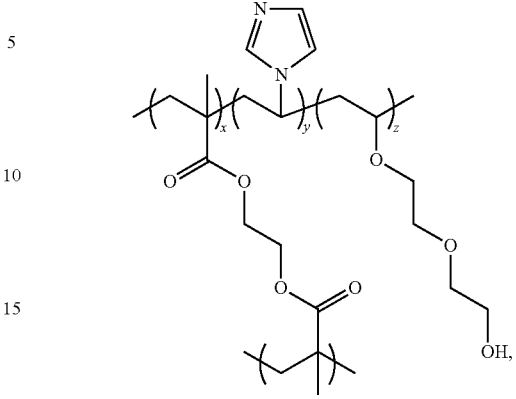

EGDMA:IM:DEG, x=60, y is a number ranging from 10-30 (e.g., 10), and z is a number ranging from 10-30 (e.g., 30).

In one aspect the release or elution of the bound one or more biological cells is accomplished in a pH range of 8-13. In another aspect a pKa value of the one or more anion-exchange resins ranges from 5.5-12, with specific ranges of 5.5-6.5, 6.5-7.5, 7.5-8.5, 8.5-9.5, 9.5-10.5, 10.5-11.5, 5.5-10.5, 8-10.5, 8-12, 10-11, and 11-12. For example, depending on the pKa values of the resin side groups, the range may be higher, e.g., the pKa values of aimidines are in the 10-11 range and the pKa values of guanidines are in the 11-12 range, which may be compatible with the growth of certain algae at higher pHs. In yet another aspect the method results in a 50-70 fold concentration of the one or more biological cells. In another aspect, when the eluting base is a calcium hydroxide (as prepared by, e.g., hydrating lime or quicklime) or magnesium hydroxide (added as a solid(s) into the liquid or in solution), the algae will spontaneously flocculate after elution and upon standing. This provides an alternative method to flocculate algae with particular benefits over current methods. In one aspect, the method further comprises the step of eluting the biological cells in the presence of a base, wherein the biological cells spontaneously flocculate after elution and upon standing. In one aspect, the method further comprises the step of eluting the biological cells in the presence of a base selected from at least one of calcium hydroxide or magnesium hydroxide, and wherein the algae spontaneously flocculate after elution and upon standing and are collected using a plate settler, a filtration system, or a partitioning system. In another aspect, the biological cell flocculation occurs concommitant with or upon release of the biological cell that has been concentrated by the resin. In another aspect, the biological cell flocculation occurs in the presence of the resin and the biological cells are separated from the water prior to elution of the biological cells from the resin. In one aspect, the method further comprises the step of eluting the biological cells from the resin in the presence of an alcohol and a base catalyst, wherein fatty acids obtained from the biological cells are directly transesterified by the alcohol leading to direct formation of the corresponding fatty acid ester. In one aspect, the method further comprises the step of eluting the biological cells from the resin in the presence of an alcohol selected from at least one of methanol, ethanol, propanol, butanol, or hexanol, and a base catalyst selected from at least one of sodium methoxide, sodium ethoxide, sodium hydroxide or potassium hydroxide, wherein fatty acids obtained from the biological cells are directly transesterified by the alcohol leading to direct formation of the corresponding fatty acid ester. In one aspect, the method further comprises the step of eluting the biological cells from the resin in the presence of an alcohol selected from at least one of methanol, ethanol, propanol, butanol, or hexanol, in the presence of an acid catalyst (e.g., sulfuric acid, hydrochloric acid, or phosphoric acid) and wherein fatty acids obtained from the biological cells are directly transesterified by the alcohol leading to direct formation of the corresponding fatty acid ester.

In yet another embodiment the instant invention provides a method of concentrating an aqueous suspension of *Neochloris oleoabundans* or *Chlorella*, or both comprising the steps of:
(i) providing the dilute aqueous suspension comprising the *Neochloris oleoabundans* or *Chlorella*, or both;
(ii) saturating an anion-exchange resin in a column or a container with the dilute suspension, wherein the anion-exchange resin has a structure given by:

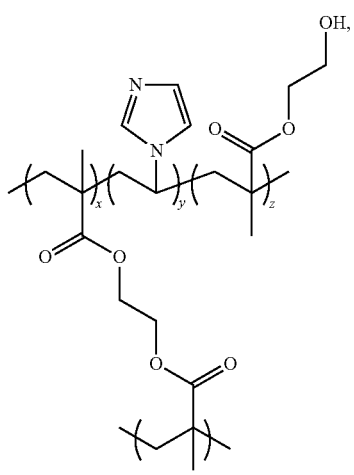

wherein x=60, y=30, and z=10;
(iii) binding the one or more *Neochloris oleoabundans* or *Chlorella* cells to the anion-exchange resin, wherein the binding is done by maintaining a specific pH;
(iv) flowing an eluent through the *Neochloris oleoabundans* or *Chlorella* saturated column to release or elute the bound *Neochloris oleoabundans* or *Chlorella* off the column by a change in the pH, wherein the change in the pH is achieved by addition of an acid, a base, or one or more chemicals; and
(v) collecting the released *Neochloris oleoabundans* or *Chlorella* cells to obtain a concentrated slurry or suspension.

The method described above further comprises the optional steps of: processing the concentrated slurry or suspension comprising the *Neochloris oleoabundans* or *Chlorella* cells in a processing unit to yield an oil or biodiesel; and reusing the anion-exchange resin to harvest or separate a subsequent batch of the one or more *Neochloris oleoabundans* or *Chlorella* cells from the slurry, or the suspension.

The present invention further includes a system for growing, harvesting, and concentrating one or more algal cells comprising: (i) a raceway pond or a growth or cultivation tank comprising one or more algal cells, wherein the tank comprises water and nutrients, and is exposed to oxygen and light to facilitate growth of the one or more algal cells, wherein the pond or the tank comprises one or more paddles, baffles, or any other agitation equipment to facilitate circulation of the nutrients and the one or more algal cells; (ii) a conveyor belt with one or more bristles or other surface modifications attached to the belt, paddles, baffles, or to the agitation equipment (any one of which can be coated with the resin) to increase a surface area of the conveyor belt or bristles, wherein the one or more bristles, belts, paddles, baffles, or other equipment or other surface modifications that provide a solid support or substrate for attachment or adsorption of the one or more algal cells; and (iii) a separation tank for harvesting or concentrating the cultivated algal cells, wherein the separation tank comprises an anion-exchange resin in solution or packed into a column, wherein the one or more algal cells are physically removed from the bristles prior to separation or the conveyor belt is cycled through the separation tank to be contacted with the anion-exchange resin, wherein the harvesting or concentration of the algal cells is achieved by a method comprising the steps of:

a) saturating an anion-exchange resin in the column or the tank with the algal cells;
b) binding the one or more algal cells to the anion-exchange resin, wherein the binding is done by maintaining a specific pH;
c) flowing an eluent through the algae saturated column to release or elute the bound algae off the column by a change in the pH, wherein the change in the pH is achieved by addition of an acid, a base, or one or more chemicals; and
d) collecting the released one or more algal cells to obtain a concentrated slurry or suspension of the one or more algal cells. Generally, the resin or resin-coated material can be cycled from the pond to the collecting tank.

In one aspect of the system the one or more algal cells comprise microalgae selected from a class comprising Bacillariophyceae, Eustigmatophyceae, and Chrysophyceae. In another aspect the microalgal genera are selected from the group consisting of *Nannochloropsis, Chlorella, Dunaliella, Scenedesmus, Selenastrum, Oscillatoria, Phormidium, Spirulina, Amphora*, and *Ochromonas*. In yet another aspect the microalgal species are selected from the group consisting of *Achnanthes orientalis, Agmenellum* spp., *Amphiprora hyaline, Amphoracoffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorellakessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia,*

*Chlorella vulgaris* var. *autotrophica*, *Chlorella vulgaris* var. *viridis*, *Chlorella vulgaris* var. *vulgaris*, *Chlorella vulgaris* var. *vulgaris* fo. *tertia*, *Chlorella vulgaris* var. *vulgaris* fo. *viridis*, *Chlorella xanthella*, *Chlorella zofingiensis*, *Chlorella trebouxioides*, *Chlorella vulgaris*, *Chlorococcum infusionum*, *Chlorococcum* sp., *Chlorogonium*, *Chroomonas* sp., *Chrysosphaera* sp., *Cricosphaera* sp., *Crypthecodinium cohnii*, *Cryptomonas* sp., *Cyclotella cryptica*, *Cyclotella meneghiniana*, *Cyclotella* sp., *Dunaliella* sp., *Dunaliella bardawil*, *Dunaliella bioculata*, *Dunaliella granulate*, *Dunaliella maritime*, *Dunaliella minuta*, *Dunaliella parva*, *Dunaliella peircei*, *Dunaliella primolecta*, *Dunaliella salina*, *Dunaliella terricola*, *Dunaliella tertiolecta*, *Dunaliella viridis*, *Dunaliella tertiolecta*, *Eremosphaera viridis*, *Eremosphaera* sp., *Effipsoidon* sp., *Euglena* spp., *Franceia* sp., *Fragilaria crotonensis*, *Fragilaria* sp., *Gleocapsa* sp., *Gloeothamnion* sp., *Haematococcus pluvialis*, *Hymenomonas* sp., *Isochrysis* aff. *galbana*, *Isochrysis galbana*, *Lepocinclis*, *Micractinium*, *Micractinium*, *Monoraphidium minutum*, *Monoraphidium* sp., *Nannochloris* sp., *Nannochloropsissalina*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrine*, *Nitzschia closterium*, *Nitzschia communis*, *Nitzschia dissipata*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Parachlorella kessleri*, *Pascheriaacidophila*, *Pavlova* sp., *Phaeodactylum tricornutum*, *Phagus*, *Phormidium*, *Platymonas* sp., *Pleurochrysis camerae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pseudochlorella aquatica*, *Pyramimonas* sp., *Pyrobotrys*, *Rhodococcus opacus*, *Sarcinoid chrysophyte*, *Scenedesmus armatus*, *Schizochytrium*, *Spirogyra*, *Spirulina platensis*, *Stichococcus* sp., *Synechococcus* sp., *Synechocystisf*, *Tagetes erecta*, *Tagetes patula*, *Tetraedron*, *Tetraselmis* sp., *Tetraselmis suecica*, *Thalassiosira weissflogii*, and *Viridiella fridericiana*. In a specific aspect the one or more algal cells comprise *Neochloris oleoabundans* or *Chlorella*.

In a related aspect the anion-exchange resin is selected from a group consisting of Formulas I to VI:

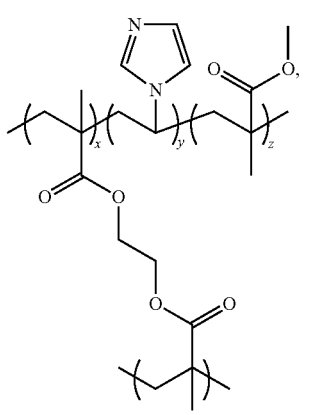

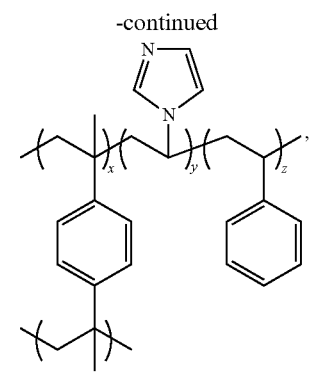

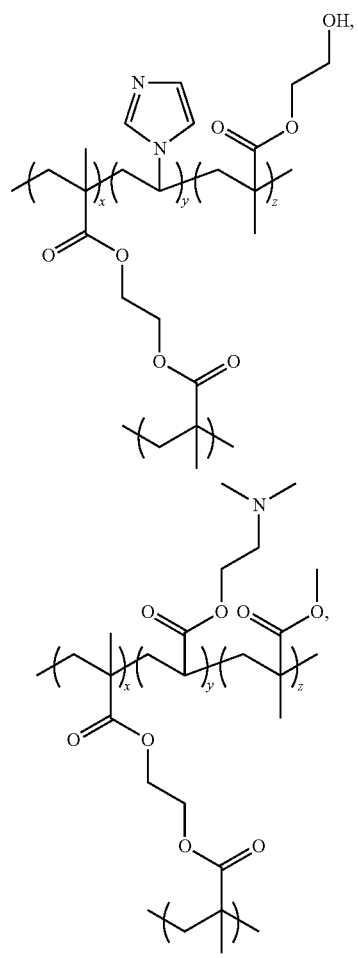

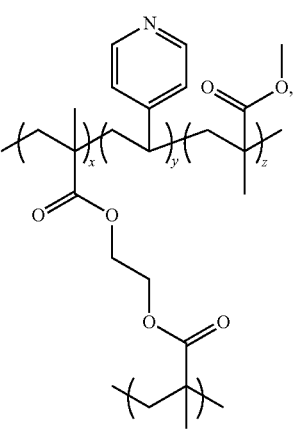

and

-continued

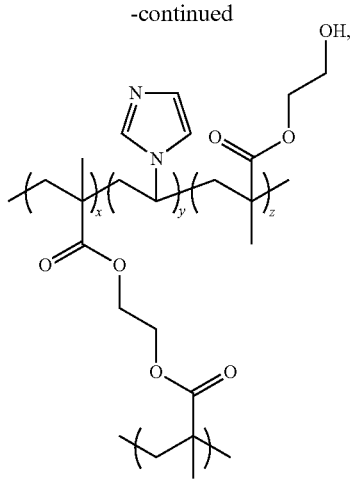

wherein x=60, y is a number ranging from 10-30, and z is a number ranging from 10-30. In one aspect the release or elution of the bound one or more biological cells is accomplished in a pH range of 8-13. In another aspect a pKa value of the one or more anion-exchange resins ranges from 5.5-12. In yet another aspect the method results in a 50-70 fold concentration of the one or more biological cells. In another aspect the method described herein further comprising the optional steps of: processing the concentrated slurry or suspension comprising the one or more algal cells in a processing unit to yield an oil or biodiesel and reusing the anion-exchange resin to harvest or separate a subsequent batch of the one or more algal cells from the slurry, or the suspension. In another aspect, when the eluting base is a calcium hydroxide solution (as prepared by, e.g., hydrating lime or quicklime) or magnesium hydroxide, the algae will spontaneously flocculate after elution and upon standing. This provides an alternative method to flocculate algae with particular benefits over current methods. In one aspect, the method further comprises the step of eluting the biological cells in the presence of a base, wherein the biological cells spontaneously flocculate after elution and upon standing. In one aspect, the method further comprises the step of eluting the biological cells in the presence of a base selected from at least one of calcium hydroxide or magnesium hydroxide, and wherein the algae spontaneously flocculate after elution and upon standing and are collected using a plate settler, a filtration system, or a partitioning system. In another aspect, the biological cell flocculation occurs solely in the presence of the resin. In another aspect, the biological cell flocculation occurs in the presence of the resin and the biological cells are separated from the water prior to elution of the biological cells from the resin. In one aspect, the method further comprises the step of eluting the biological cells from the resin in the presence of an alcohol and a base catalyst, wherein fatty acids obtained from the biological cells are directly transesterified by the alcohol leading to direct formation of the corresponding fatty acid ester. In one aspect, the method further comprises the step of eluting the biological cells from the resin in the presence of an alcohol selected from at least one of methanol, ethanol, propanol, butanol, or hexanol, and a base catalyst selected from at least one of sodium methoxide, sodium ethoxide, sodium hydroxide or potassium hydroxide, wherein fatty acids obtained from the biological cells are directly transesterified by the alcohol leading to direct formation of the corresponding fatty acid ester. In one aspect, the method further comprises the step of eluting the biological cells from the resin in the presence of an alcohol selected from at least one of methanol, ethanol, propanol, butanol, or hexanol, in the presence of an acid catalyst (e.g., sulfuric acid, hydrochloric acid, or phosphoric acid) and wherein fatty acids obtained from the biological cells are directly transesterified by the alcohol leading to direct formation of the corresponding fatty acid ester.

BRIEF DESCRIPTION OF THE DRAWINGS

For a more complete understanding of the features and advantages of the present invention, reference is now made to the detailed description of the invention along with the accompanying figures and in which:

FIG. 5B shows the concentration and recovery of KAS 603 as a function of elution volume for EGDMA: IM:HEMA (60:30:10 w/w/w). Each resin sample was loaded with algae from 500 mL of dilute suspension (0.2 g L21), eluted with progressively smaller volumes of pH 12 sodium phosphate solution (50, 25, 10, or 5 mL), and measured for the amount of algae released and retained in the resin bed for each elution volume;

FIGS. 7A-7F show the structures of pH-dependent reversible algal binding resins for use with the present invention.

DETAILED DESCRIPTION OF THE INVENTION

Figure 1A:
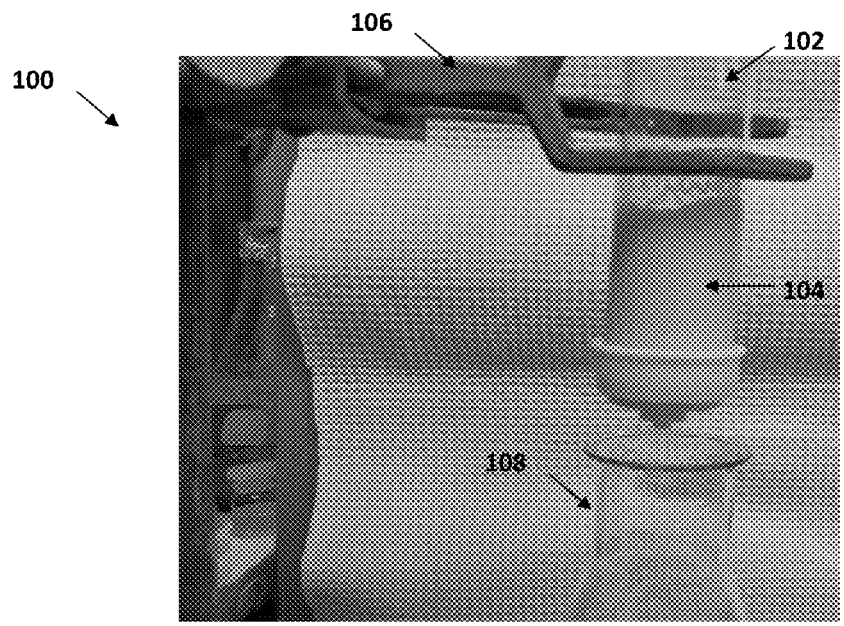
FIGS. 1A-1D are photographic images showing the algal binding and release assay. Resin column (FIG. 1A) is loaded with algal suspension as algae is bound to the resin, the clear growth media is recovered (FIG. 1B). After binding saturation, regeneration buffer is used to release algae from the resin (FIG. 1C). The resin is cleared and reused for another load of algae (FIG. 1D)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Abbreviations: AIBN azobisisobutyronitrile, BW brackish water (approx. 5 psu), DCW dry cell weight, DEG di(ethylene glycol) vinyl ether, DMA dimethylamine methacrylate, DVB divinyl benzene, EGDMA ethylene glycol dimethacrylate, FW freshwater (approx. 7 psu), HEMA 2-hydroxyethyl methacrylate, IM vinyl 2-imidazole, KAS algal species KAS 603, MMA methyl methacrylate, Neo *Neochloris oleaoabundans*, OD optical density, psu practical salinity units, PYR vinyl 4-pyridine, S styrene, SW saltwater (approx. 32 psu).

As used herein the term "algae" represents a large, heterogeneous group of primitive photosynthetic organisms, which occur throughout all types of aquatic habitats and moist terrestrial environments. Nadakavukaren et al., Botany. An Introduction to Plant Biology, 324-325, (1985). The term "algae" as described herein is intended to include the species selected from the group consisting of the diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis* and *Pleurochysis*.

The algal cells described hereinabove are selected from a division comprising *Chlorophyta, Cyanophyta* (Cyanobacteria), *Rhodophyta* (red algae), and *Heterokontophyt*. The one or more algal cells comprise microalgae selected from a class comprising Bacillariophyceae, Eustigmatophyceae, and Chrysophyceae. The microalgal genera are selected from the group consisting of *Nannochloropsis, Chlorella, Dunaliella, Scenedesmus, Selenastrum, Oscillatoria, Phormidium, Spirulina, Amphora,* and *Ochromonas*. In yet another aspect the microalgal species are selected from the group consisting of *Achnanthes orientalis, Agmenellum* spp., *Amphiprora hyaline, Amphoracoffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorellakessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Effipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff *galbana, Isochrysis galbana, Lepocinclis, Micractinium, Micractinium, Monoraphidium minutum, Monoraphidium* sp., *Nannochloris* sp., *Nannochloropsissalina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheriaacidophila, Pavlova* sp., *Phaeodactylum tricornutum, Phagus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana*.

The present invention discloses a method of using a resin to bind algae for the purpose of harvesting and concentrating algae from dilute suspensions. As used herein, the term "resin" refers to the chemical composition, not the physical form of the polymers of the present invention. The resin of the present invention can be made into a variety of physical forms, including but not limited to, a resin bead, string, mesh, film, coating, filter, cylinder, sponge, plate, screen, or belt; whether in generally two or in three dimensions. In one example the resin is formed into, or coated in or onto, a belt for harvesting. Thus, the resin polymers of the present invention can take a variety of physical forms such as particles, films or coatings. For example, one can modify the methacrylate or divinylbenzene resin with polyvinylimidazole groups that form ionic bonds with the algal cell surface groups when in a neutral to acidic pH environment. Thus, binding of the biological cells occurs when the environment is at a pH below the pKa of the weak base functionality of the resin. By way of explanation, generally, the pKa is the pH where the amine is ½ in the neutral state and ½ in the (+) positive charged state. As the pH is lowered below the pKa, more and more of the amine groups become (+) positively changed until essentially 100% of the amines are protonated (ammonium form). As the pH of the media is raised above the pKa, the ammonium form loses protons (H+) and becomes uncharged. Therefore, biological cells such as negatively charged algae no longer bind. Bound algae are released from the resin when the pH of the resin environment is changed such that the algae no longer bind.

Current technology for algae harvest and concentration include centrifugation, which is effective but requires pumping the algae and has high capital and operating cost; or chemical flocculation, which is generally effective but requires pumping the algae as well as considerable chemical costs and can lead to the formation of irreversibly bound algal aggregates [15]. The present invention offers a low cost, reusable material that can be used during cultivation to continuously harvest algae by harvesting the resin for further processing.

The algae must grow in dilute concentrations in order to receive adequate light perfusion. Therefore, water transport and removal is a contributor to the high cost of algae biofuel production. The invention described herein can be used in harvesting applications involving very little to no energy input, reducing overall production costs, Using resins to harvest algae as described herein potentially avoids pumping large amounts of water that is normally required for other algal harvesting methods. The resin of the present invention is enclosed in porous containers, packed into a column, attached to a substrate, belts with fibers, or other high surface area presentations that concentrate the algae from dilute suspensions. The containers then can be harvested and the algae eluted in concentrated form. The resins are reusable and easily separable from the algae.

The algae must be within a certain distance of the resin in order to bind; this can be addressed by the present inventors by either continuously circulating the algae, or moving the resin through the algae. Binding capacity of the resin is determined by the density and spacing of functional groups on the resin, and the binding surface area; increasing the composition of functional groups within the resin and using resin geometries that further expose binding sites can improve overall algae binding capacity. Once bound to the resin, the algae can be treated by solvents in order to lyse the cell wall and digest the algae. The resins can be used in water treatment in order to remove unwanted microbes.

Algae have great potential as a source of biofuel but at present, growth and processing are prohibitively expensive. Harvesting algae is particularly costly because it normally involves pumping large amounts of water. In an effort to explore less expensive methods for harvesting the present inventors have developed resins that bind and release algae as a function of pH. The inventors developed a series of weak anion exchange resins incorporating various functional base groups with different pKa values. Each resin was analyzed to determine its algal binding capacity and binding reversal as a function of pH. The present inventors have obtained resins that bind 10% algae by weight and essentially 100% release when the pH was raised.

Algae have the potential to address current and future energy needs as feedstock for biofuels [1]. High oil content and biomass production rates [2], as well as higher photosynthetic efficiencies than terrestrial plants [3], make algae ideal for commercial-scale biofuel production. Algae consume carbon dioxide, thus reducing greenhouse gas emissions, and can improve energy cost balances when using flue gas as a carbon source [3]. Furthermore, algae can be cultivated in brackish water unsuitable for agricultural crops, and used to remediate wastewater [4]. Finally, in addition to fuel, profitable co-products can be generated, such as animal feed, biopolymers, and agricultural fertilizers [5].

One of the current barriers to using algae for biofuel is the cost of growing and harvesting algae from dilute suspension. Most algae used for biofuel are small, 2-3 micrometers in diameter, and are difficult to separate from water by filtration or tank settling [6]. Furthermore, autotrophic algal growth density is limited by light perfusion. While lab-scale studies report biomass density in the magnitude of grams per liter media [7], large-scale cultivation, such as in a raceway pond, often produce biomass concentrations of less than 0.5 g/L [1]. As a consequence, large volumes of water must be processed in order to generate the amount of biomass needed. For example, to recover just one kilogram of algal dry mass from an algal culture of 0.4 g/L density (a typical biomass density observed in our photobioreactors), at least 2500 liters (660 gallons) of water must be processed. Previous studies have shown that biomass recovery contributes 20-30% of the total production costs [8]. Thus, the cost of water removal from algal biomass poses a significant obstacle to the expansion of algae-based bioenergy [6].

As used herein, the term "flocculation" refers to a process of contact and adhesion in which the particles of a dispersion form larger-size clusters, e.g., in the flocculation of a microbe (e.g., yeast) when exposed to an alkali environment or the presence of sugar. A related term is "bulk autoflocculation" in which clumps of the microbe result from raising the pH of large volumes of, e.g., algal cultures, such as a growth pond in order to precipitate and harvest the algae.

Current techniques used on the commercial production scale have proven inadequate, requiring considerable time or energy expenditure to harvest the algal biomass. Mechanical separation methods such as centrifugation produce the highest biomass yields, but also have high equipment and energy costs [8, 9]. Flocculation, the induction of algal cell aggregation, can be achieved by either charge neutralization or addition of charged polymers that coordinate the charged algal surfaces. Although operating cost can be low, depending on the flocculant, it involves continual addition of chemicals to treat the entire volume of algae to be harvested. Some of these flocculants or treatments such as high pH may cause product decomposition whereas others may have long residence times and, in any case, can affect the output water [3]. Experimental harvesting techniques, such as ultrasound-induced aggregation, have been effectively demonstrated at the laboratory scale, but have been projected to be more expensive than current centrifugation techniques [10].

Problems with the current methods led the present inventors to design, develop, and test reusable resins for concentrating algae out of suspension. The strategy takes advantage of the negative surface charge on algae, which bind to weak anion exchange resins as a function of pH. While simple in principle, the performance of these resins was complicated by non-specific or non-pH dependent binding, as well as differences in binding capacity. Studies presented herein describe the binding capacity and algal release as a function of resin chemistry. Through several generations of synthesis and analysis the inventors were able to progressively improve both binding capacity and release properties of the resins. The best of these resins can bind ten percent of their weight in algae with essentially 100% reversibility and the ability to concentrate algae more than 50-fold from dilute suspension.

Materials and Methods: Amberlite® IRA-67, Aminomethyl Chemmatrix®, Celite 500, Dowex® Marathon™ WBA free base, Dowex® Retardion 11A8, Levatit® MP-62 free base, poly(4-vinylpyridine hydrochloride), polymer-bound aniline, Sephadex™ G-25, Stratospheres™ PL-DETA, Stratospheres™ PL-DIPAM, Stratospheres™ PL-PPZ, and polymer-bound TETA were obtained from Sigma (St. Louis, Mo.). Amberlite® CG-400 was obtained from Mallinickrodt (St. Louis, Mo.). DEAE Sephadex™ was obtained from Pharmacia Biotech (Sweden). Silica gel was obtained from EMD Chemicals (Gibbstown, N.J.). Dimethylaminoethyl methacrylate (DMA), divinylbenzene (DVB), ethylene glycol dimethacrylate (EGDMA), methyl methacrylate (MMA), styrene (S), vinyl 2-imidazole (IM), vinyl 4-pyridine (PYR), 2-hydroxyethyl methacrylate (HEMA), and azobisisobutyronitrile (AIBN) were obtained from Sigma.

*Neochloris oleoabundans* (UTEX LB 1185) was obtained from The University of Texas at Austin Culture Collection of Algae (Austin, Tex.). KAS 603, a saltwater species of *Chlorella*, was obtained from Kuehnle Agro Systems (Hawaii).

Algal cultivation and harvest: *Neochloris oleoabundans* was cultivated in freshwater (approximately 5 psu) Bold 3N (B3N) medium [11], and *Chlorella* sp. was cultivated in saltwater (approximately 35 psu) f/2 medium [12]. Both cultures were grown at room temperature (23° C.) under cool white fluorescent lights on a 12 h:12 h, light:dark photoperiod in airlift photobioreactors aerated with ambient air using aquarium pumps. Immediately prior to testing, algae were concentrated by centrifugation (Sorvall Legend XTR) at 8000 RPM for 10 min. The supernatant was decanted and the pellet resuspended in B3N medium at concentration of 0.2 g/L. Media was tested at freshwater salinity level (5 psu) and pH 6.5, unless otherwise noted.

Commercial resin testing: Commercially available resins were evaluated for the ability to bind and release algae. For each assay, 100 mg of washed resin was loosely packed into a polyethylene column. 100 mL of algal suspension at 0.2 g/L was loaded into the column until the resin reached binding saturation. The optical density of the algal suspension at 680 nm ($OD_{680}$) loaded onto the column and recovered in the eluate was measured for quantifying binding capacity. The resin was rinsed with distilled water, and then eluted with 10 mM sodium phosphate at pH 12 to release algae.

Resin synthesis: Monomers were combined in ratios based on weight as indicated in FIGS. 7A-7F. EGDMA- and DVB-crosslinked resins were synthesized with functional monomers DEG, DMA, IM, PYR, and HEMA. The remainder of resin weight was occupied by spacer monomers: MMA for EGDMA resins, or S for DVB resins. An equivalent volume of solvent was added to the combined monomers, consisting of 50% toluene and 50% acetic acid:water (1:30 v/v). Porosity of the crosslinker network was held relatively constant by keeping solvent at the same volume percentage for all resins, though the porosity of these materials could not be measured to confirm their consistency. In general, porosity should be avoided if the space is occupied by water and not a biological cell that binds the resin. Resin synthesis was carried out in round bottom flasks fitted with an argon bubbler and heated to 60° C. with constant stirring. Polymerization was initiated by addition of 1 mol % AIBN and polymerization continued until the mixture formed a brittle solid. The polymer was then dried in 55° C. oven for 12 h, scraped from the flask and ground by mortar and pestle. The crushed resin was then sized between 35 and 170 size stainless steel meshes to obtain particles of ~100-500 μm diameter. Before use, the resin was washed with distilled water.

Determination of algal dry cell weight: Routine determination of algal dry cell weight (DCW), was obtained by measuring $OD_{680}$ using a Shimadzu spectrophotometer. To convert $OD_{680}$ to DCW, the $OD_{680}$ was recorded for an algal dilution series and then the contents of each cuvette was collected onto pre-weighed cellulose acetate membranes (Pall Co., Port Washington, N.Y.). The membranes were then dried in a vacuum oven (15 in. Hg., 60° C.) for 12 h and then weighed to give the DCW for a given $OD_{680}$. To avoid optical filtering effects, algal suspensions were diluted, if need be, to keep the $OD_{680}$ under 1.8.

Algal binding and release assay: To test algal binding capacity and release characteristics of newly synthesized resins, 1 g of resin was added to 100 ml of 0.2 g/L algal suspension in a 250 ml flask. The suspension was then gently agitated on an orbital shaker (VWR, 125 RPM) for 15 min. Subsequently, the suspension was filtered through #170 stainless steel mesh to isolate the resin and the $OD_{680}$ of unbound algae was measured. The difference in $OD_{680}$ obtained before and after resin binding was used to determine how much algae was bound to the resin. The resin was then transferred to a second flask containing 100 mL of 10 mM sodium phosphate buffer at pH 12 and the mixture was again agitated for 1 h. The resin was then removed by filtration through the steel mesh and $OD_{680}$ of desorbed algae was recorded. To determine the pH dependence of algae unbinding, the same procedures were carried out except that algae were eluted using 100 mL of 10 mM sodium phosphate buffer adjusted to have a pH over the range of 8-12.

To determine how well resins could concentrate algae, the procedures were the same as for the previous elution studies except that 1 g of resin was added to 500 mL of 0.2 g/L algal suspension in a 1 L flask. Algae were then eluted off the resin with different volumes (500, 50, 25, or 10 ml) of 10 mM sodium phosphate buffer at pH 12.

Figure 1B:
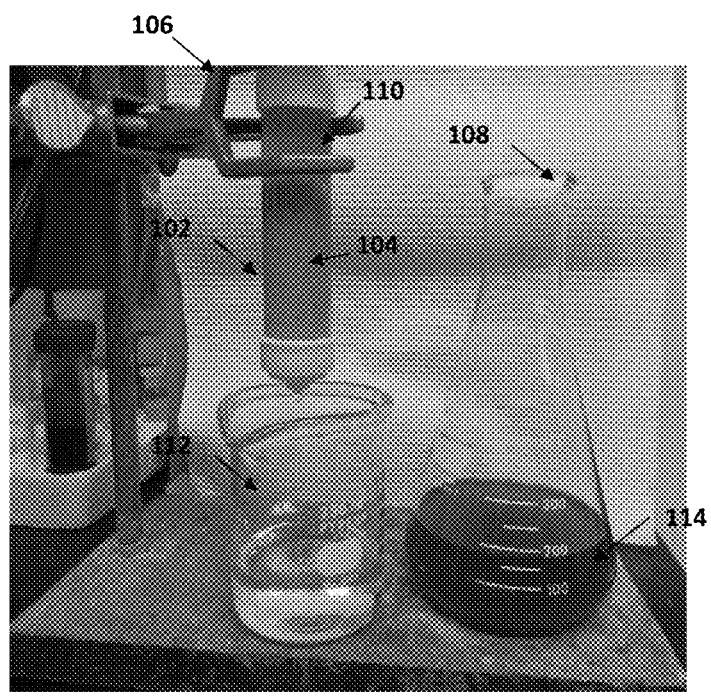
Figure 1C:
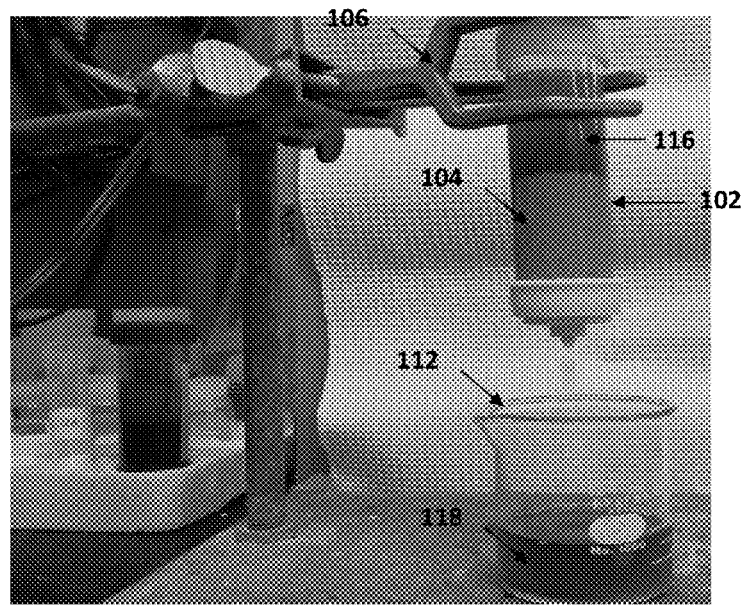
Figure 1D:
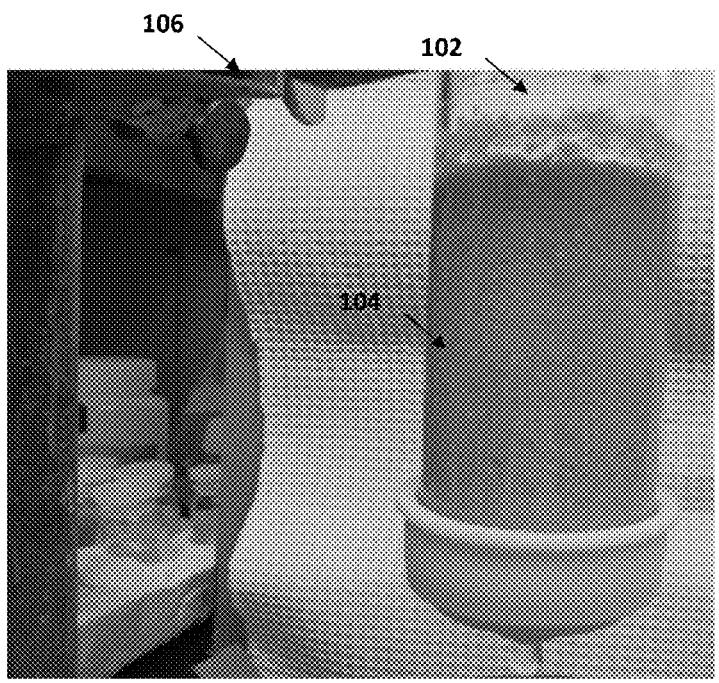

FIGS. 1A-1D are photographic images 100 showing the algal binding and release assay. Resin column 102 (FIG. 1A) is loaded with algal suspension 110 as algae is bound to the resin 104, the clear growth media 114 is recovered (FIG. 1B). After binding saturation, regeneration buffer 116 is used to release algae 118 from the resin 104 (FIG. 1C). The resin 104 is cleared and reused for another load of algae 110 (FIG. 1D). Studies were based on samples run in triplicate at the same time. Mean DCW bound and released per gram resin was reported, with brackets indicating standard error of the mean.

In order to quantify masses of algae bound and desorbed from the resin by optical measurement, chlorophyll optical density calibrations were determined for both algal species. The calibration fits were linear over the optical density range tested ($R^2_{Neo}=0.997$, $R^2_{Chl}=0.999$) (data not shown). DCW obtained by optical measurement was validated against gravimetric measurement of original algal suspension and released algae.

Previous studies had shown that strong anion exchange resins could bind algae. However, once algae bound to the resin, they could only be eluted by extreme conditions. This could be due to the fixed charge on the resin but it might also be due to other interactions between the resin and the algal surface. For example, the results shown in Table 1 indicate that Amberlite CG-400 and IRA 67, DEAE Sephadex, polymer-bound pyridine, and aminomethyl Chemmatrix were able to bind algae, but algae could not be removed by base. On the other hand, a number of resins and chromatography materials including Dowex Marathon WBA and Retardion 11A8, Levatit MP-62, Celite, silica gel, and Sephadex did not bind to algae even though some of them are anion exchange resins. A few of the resins, TETA resin, Stratospheres resins PL-PPZ, PL-DETA, and PL-DIPAM, and polymer-bound aniline, did show some ability to bind and release algae.

TABLE 1

Evaluation of commercial resins.

| Resin | Functionalization | Algal binding | Algal release |
|---|---|---|---|
| Polymer-bound TETA | triethylene tetramine | + | + |
| nitrocellulose | nitrate | + | + |
| Stratospheres PL-PPZ | piperazine | + | + |
| Stratospheres PL-DETA | diethyethylene triamine | + | + |
| Stratospheres PL-DIPAM | diisopropyl ethylamine | + | + |
| Polymer-bound aniline | aniline | + | + |
| Amberlite CG-400 | quaternary ammonium | + | − |
| DEAE sephadex | diethylamine | + | − |
| Amberlite IRA 67 | amine | + | − |
| Poly(4-vinylpyridine HCl) | pyridine | + | − |
| Aminomethyl Chemmatrix | amine | + | − |
| Dowex Marathon WBA | amine, weak base | − | n/a |
| Dowex Retardion 11A8 | paired anion and cation sites | − | n/a |
| Levatit MP-62 | weak base | − | n/a |
| Celite 500 | none | − | n/a |
| Silica gel | none | − | n/a |
| Sephadex G-25 | none | − | n/a |

Based on the results obtained with commercial resins, the inventors hypothesize that weak anion exchange resins showed the most promise but the resin matrix was also important. Furthermore, we suspected that those with pKa values near 7 would be easier to elute than those with high pKa values. The choice of resin (amine functionality of the resin) can depend on the pH of the growth media. Generally, a resin is selected with a pKa such that the resin is (+) positively charged at the pH of the growth media. For example, Imidazole has a pKa of around 8, therefore, one would have to grow algae at pH 8 or less. The pH at which algae is grown can vary and often has a high pH. The present inventors have generated a series of resins incorporating one of three different functional groups. These functional groups in order of increasing pKa, are pyridine (PYR), imidazole (IM), and dimethylamine (DMA), (FIGS. 7A-7E).

Figure 2:
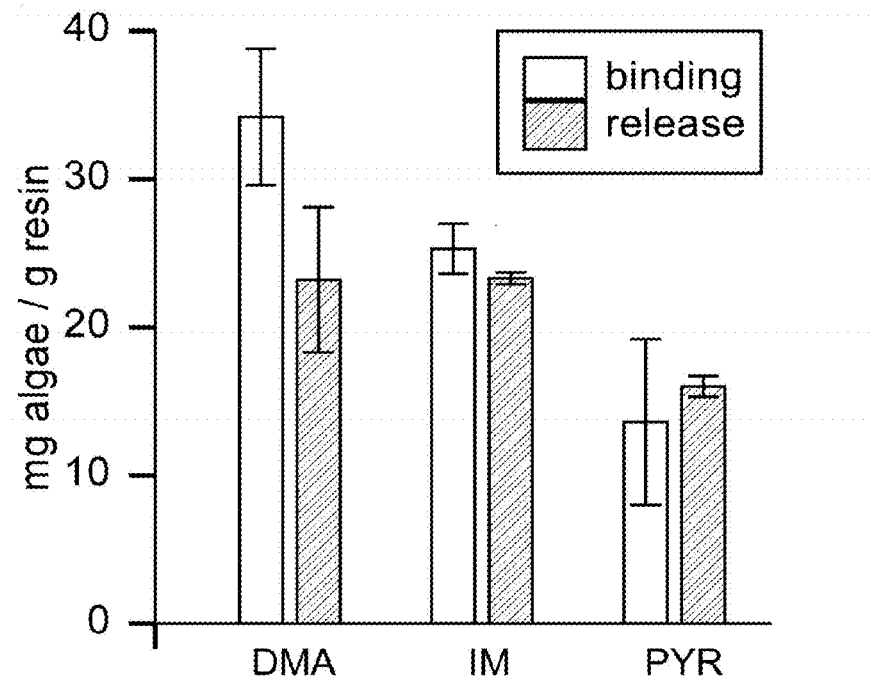
FIG. 2 is a plot showing algal binding by resin functional group. Comparison of weight of algae bound and released per gram of resin for dimethylamine (DMA), imidazole (IM), and pyridine (PYR) resins.

The binding capacity and adsorption reversibility was tested for DMA, IM, and PYR incorporated at 10% wt into PMA resin (FIG. 2). Higher binding capacity was observed for DMA and IM resins, with 34.2 and 25.3 mg of algae bound per gram of resin, respectively, while PYR was less at 13.6 mg. After algae release at pH 12, 23.2 (68% of bound algae released), 23.3 (92%), and 16.0 mg algae per g resin (100%) was unbound from DMA, IM, and PYR, respectively.

Figure 3:
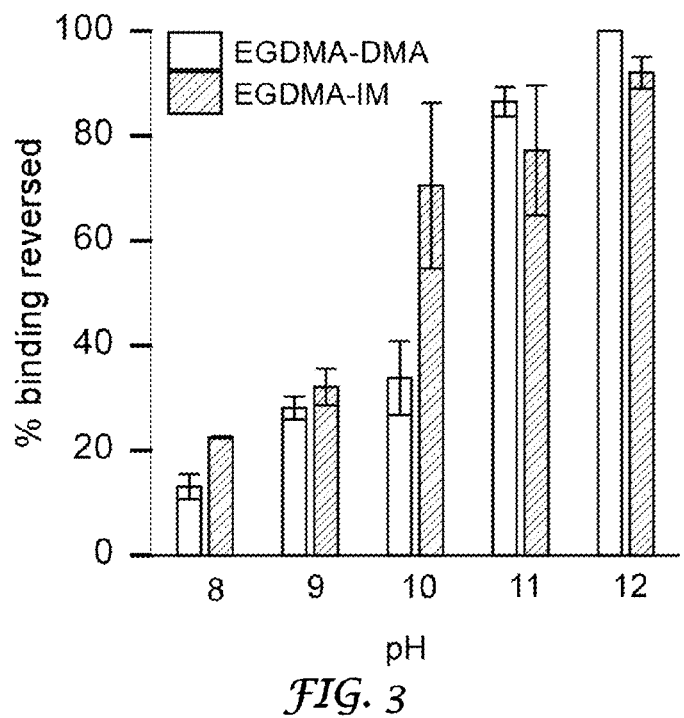
FIG. 3 is a plot showing removal of algae over a range of pH. Binding reversibility of DMA and IM resins in regeneration buffers, pH 8-12.

The initial binding and release data showed that binding capacity correlated positively with increasing pKa of the weak base component while reversibility correlated inversely with pKa. Binding reversibility was further examined for DMA and IM resins by desorbing algae over a range of pH values. The proportion of algae released at each pH is shown in FIG. 3. At lower pH 8 and 9, algae remain largely fixed to both resins. For DMA resin, 13.1% and 28.1% of bound algae was released at pH 8 and 9, respectively, while for IM resin, 22.5% and 32.1%. At pH 10, DMA released 33.8% of algae back into suspension, while IM released 70.5%. When pH was increased to 11 and 12, algal binding was mostly reversed, with DMA resin releasing 86.5% and 100% of algae from the resin, and IM resin releasing 77.2% and 92%.

Figure 4A:
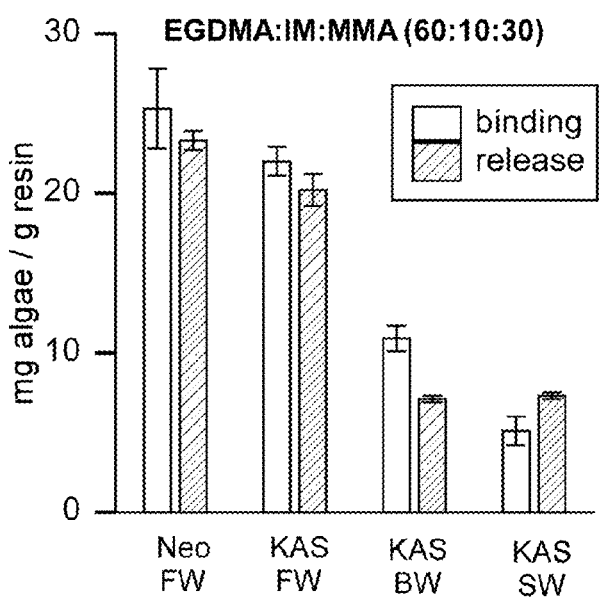
FIGS. 4A and 4B are plots showing algal binding in different growth media. Comparison of weight of algae bound and released per gram of resin for IM resin using *Neochloris* in B3N medium, and *Chlorella* in freshwater, brackish, and saltwater salinity f/2 medium using PMA resin (FIG. 4A), and PS resin (FIG. 4B)
Figure 4B:
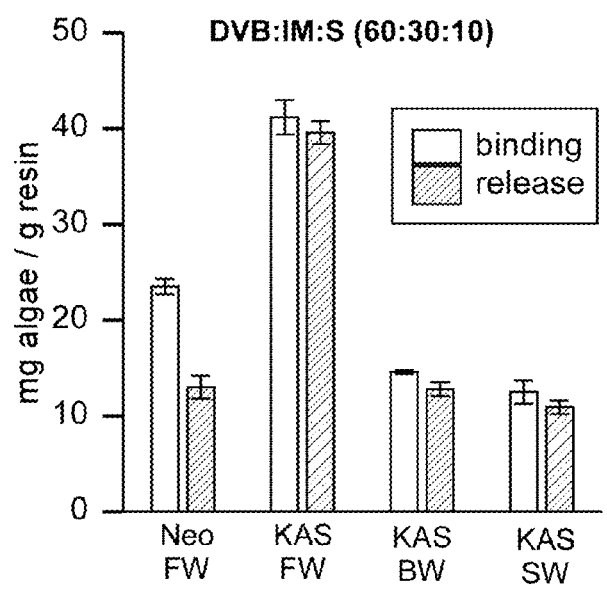

Having observed that the IM functional group was effective at both binding and releasing algae, the effect of resin crosslinker was examined. When IM was incorporated into PS resin at 60:10:30 w/w/w ratio of DVB:IM:S the algae bound poorly. However when the ratio of IM was increased to 60:30:10 w/w/w DVB:IM:S, binding was comparable to that of the methacrylate resin. The inventors then compared IM incorporated into PMA resin (EGDMA:IM:MMA, 60:10:30 w/w/w) to the PS resin (DVB:IM:S, 60:30:10 w/w/w). For these comparisons, the inventors assayed the binding of Neochloris in freshwater B3N medium and Chlorella in freshwater, brackish, and saltwater f/2 media (7, 15, and 32 psu). The results show that PMA resin (FIG. 4A) had the highest binding capacity for Neochloris (34.2 mg algae per g resin) whereas binding for Chlorella was considerably lower in fresh water (12.8 mg/g) and decreased even further in brackish (10.9 mg/g) and sea water (5.1 mg/g). The PS resin (FIG. 4B) was found to have a higher binding capacity for Chlorella in freshwater medium (41.2 mg/g) than Neochloris (23.5 mg/g). As with the PMA resin, Chlorella binding capacity was reduced at medium and high salinity (14.6 mg/g, 12.5 mg/g).

The data presented herein shows that binding of algae to some of these resins was not 100% reversible and that there was some binding that was not simply due to the charge on the resin. To study this further, other resin compositions were also tested. Interestingly, the inclusion of HEMA in the resin improved both binding capacity and reversibility. Initial studies showed that EGDMA:IM:HEMA, 60:30:10 w/w/w had a binding capacity of 91.0 mg/g resin and essentially 100% reversibility with Chlorella in freshwater medium. Removal of algae was tested with decreasing volumes of releasing buffer in order to determine if the resins could yield a more concentrated algae solution after binding.

Figure 5A:
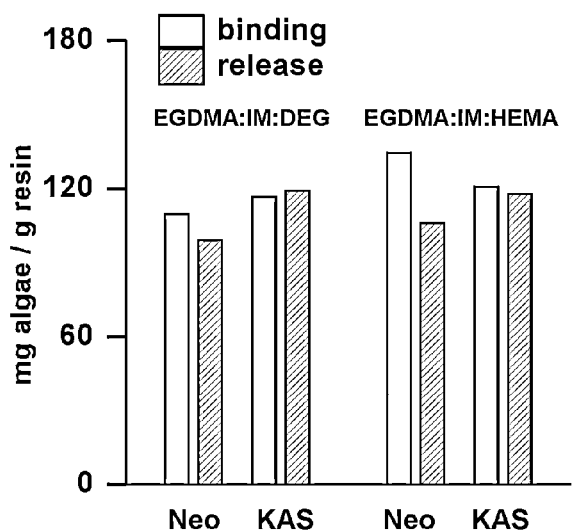
FIGS. 5A and 5B show the Improved binding properties of resins containing EGDMA:IM:HEMA (60:30:10 w/w/w) or EGDMA:IM:DEG (60:30:10 w/w/w) (FIG. 5A). Resins were prepared and tested for binding capacity and algae release at pH 12 for *Neochloris* in B3N medium, and for KAS 603 in f/2 medium at 5 psu.
Figure 5B:
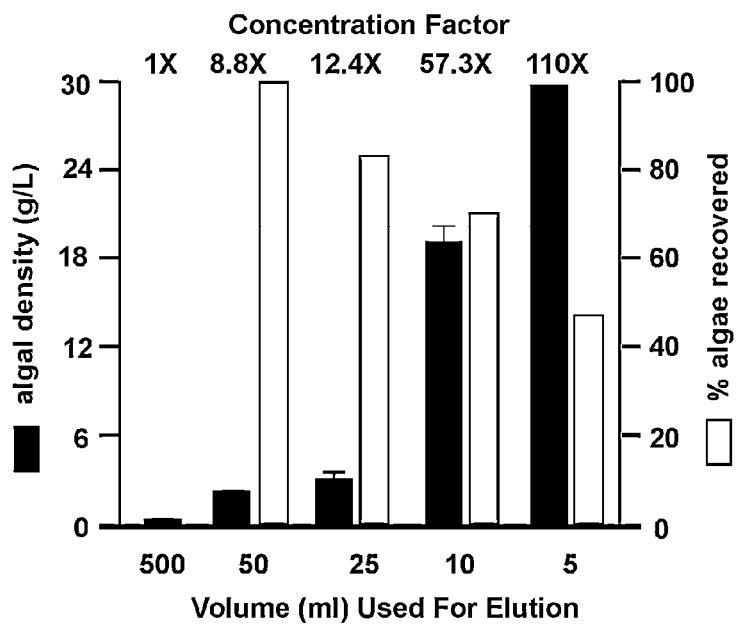

FIGS. 5A and 5B shows that after binding, comparable amount of algae can be released. After exploring algal binding behavior at lower monomer composition, a resin with higher binding capacity was developed. Having shown that increasing the percentage of IM functional group improved the binding capacity of DVB resin, similarly the amount of IM was increased to 30 wt % for EGDMA resin. While this also increased binding capacity for both algal species, a larger fraction of the algae now bound irreversibly. In addition, previous results showed that Neochloris was often difficult to completely remove from the resin, even at 10 wt % IM. However, through testing a number of other functional groups, it was found that inclusion of either DEG or HEMA in EGDMA resin with 30 wt % IM resulted in a high capacity, reversibly binding resin. For EGDMA:IM:DEG (60:30:10 w/w/w), binding to Neochloris increased to 109.6 mg g$^{-1}$ resin while for EGDMA:IM:HEMA (60:30:10 w/w/w), binding increased to 134.4 mg g$^{-1}$ resin. Raising the pH to 12 released 90 and 80% of the bound algae, respectively (FIG. 5A). Binding capacity for KAS 603 also increased for both EGDMA:IM:DEG (116.7 mg g$^{-1}$) and for EGDMA:IM:HEMA (120.7 mg g$^{-1}$). Furthermore, after raising the pH to 12 essentially 100% of the bound algae were released from both resins. In the studies hereinabove, binding reversibility was measured using large volumes of media such that entrapment of algae in the resin bed, as opposed to binding, was not an issue. However, to be useful for harvesting it is important to show how well resins can actually concentrate algae. To confirm this, a set of EGDMA:IM:HEMA resin samples (FIGS. 7A to 7F) were prepared and each sample was mixed with 500 mL of 0.27 6 0.04 g L21 KAS 603 algae. Once the algae were bound, resin samples were collected on a filter and eluted with different volumes of pH 12 sodium phosphate solution (500, 50, 25, 10, or 5 mL). The results (FIG. 5b) show that with successively smaller volumes of solution, the concentration of algae in the eluate increased. As expected, as the volume of elute decreased, increasing amounts of algae were trapped in theresin bed. To show that this was merely entrapment rather than binding, once samples of the initial eluate were taken for measurement, washing the resin bed with distilled water (~10-20 mL) in each case removed all the remaining algae.

Resin design: Commercial anion exchange resins were effective at binding algae out of suspension, however the binding capacity was, for all resins that bound algae, typically low and for some of them, binding was not easily reversed. The commercial resins that we tested herein are marketed for a broad array of applications, including chemical purification, water treatment, and polymer-supported synthesis, and were selected based on amine or base surface functionality that could potentially interact with the algae. As a control, materials without surface functionality, such as silica, were tested, and it was confirmed that no algal binding occurred. In addition, some resins with weakly anionic groups, such as Dowex Marathon WBA and Retardion 11A8, were unable to bind algae at all. Strongly basic resins, such as Amberlite CG-400, were able to bind algae out of solution, binding approximately 30 mg of algae per g of resin, but binding could not be reversed by elution with buffers up to pH 12. Resins for polymer-supported chemistry, such as Stratospheres PL-PPZ, PL-DETA, and PL-DIPAM, were successful at both binding and releasing the algae. However, algal binding capacity was very low, less than 10 mg of algae per g of resin. Also, since these resins are manufactured for niche market, they are only available for purchase at small quantities for high cost. The resins synthesized by the present inventors had a high crosslinker density, and proved to be non-swelling, hard resins suitable for testing.

The polymer resin's ionic functional group was expected to be the main alga-interacting component, similar to anion exchange resin. Algae are unicellular plants with cell walls composed of biopolymers, which have carboxyl groups that are ionized at the pH of the media [14]. Since these carboxyl groups are common to all algae, the polymer resin harvest techniques can be applied to all algal cultures. The ionic content of seawater reduced binding.

With greater difference between the media pH and the functional group pKa, an improvement of binding capacity was observed. DMA, with a pKa of 10.2, consistently demonstrated high binding capacity, and IM, with pKa 7.5, also bound algae reasonably well. The PYR resin with pyridine functional groups having a pKa of approximately 5.5 was also the weakest binding resin. This is to be expected since the pH of media is above the pKa and only a fraction of the pyridines should be ionized.

From the various tests, IM was favored over DMA because of its better binding reversibility at lower pH. Because of IM's lower pKa value, it could be reverted to a non-ionized form with less of a pH shift than DMA. The fact that the majority of algae was released at pH 10 for IM resin while for DMA required at least pH 11 in to release most of the algae is significant in terms of the practical application. While a shift of one pH order seems small on a laboratory scale, in an industrial process it would require ten-fold more base.

Interestingly, while control PMA and PS resins without ionic functional groups did not exhibit algal binding behavior, the inventors found that the choice between PMA and PS did subtly affect the overall binding capacity of the functionalized resins. The observed difference in binding capacity may be related to the hydrophilicity of the crosslinker and spacer groups. The PMA resin consists of hydrophilic monomers that make the resin more wettable, facilitating the interaction between the ionic functional groups and the algal surface. When the MMA spacer was replaced by HEMA, the hydroxyethyl group in the latter resin increased the hydrophilicity of the resin, and the binding capacity also increased. In contrast, the PS resin consists of hydrophobic monomers that weakly repel the algae. It was possible to obtain PS resins that showed similar binding capacities to the PMA resin but it required three times higher concentrations of the IM monomer. Also, irreversible binding between *Neochloris* and PS resin was observed, indicating that some algal species have hydrophobic surface groups that interact strongly with hydrophobic polymers and can lead to resin fouling.

Biomass harvesting and quantitation: Initially, assays were conducted in upright resin-filled columns. This proved to be problematic, in that the resin could pack unevenly, leading to channeling within the column. This approach resulted in an uneven column flow rate, a variable affecting resin residence time, and the binding and release behaviors. In addition, the column frit rapidly accumulated a layer of desorbed algae that further impeded flow, especially during concentration studies when a minimum amount of buffer was used for elution. The algae binding and release experiments conducted in flasks resulted in more reproducible adsorption and desorption results.

Optical chlorophyll measurements were used to expedite the resin screening process, and were used as an indication of viable cells with higher specificity than measuring algal DCW using a gravimetric method. The optical chlorophyll measurements and the gravimetric measurements performed on a sample of the released algae were found to be comparable.

While the resin binding and percent release of algae from the resin was measured under equilibrium conditions these measures do not necessarily reflect how they would actually be used to harvest algae. Thus, a study was conducted to determine if algae could be completely recovered off the resin using smaller volumes of buffer solution. 50-fold concentration was easily obtained with our assay, yielding a slurry of 19 g/L biomass density and in one study 100 fold concentration was obtained. However, using resin beads for these assays, as one elutes with less solution, the algal eluate becomes more concentrated but less than 100% of the algae is eluted off the resin. This is because some algae becomes entrained with in the spaces between the beads. Under these conditions, when the initial elutions were followed with additional eluent, 100% elution of the algae was still observed. Alternatively, it was found that batches of algae could be bound to the resin, and then eluted repeatedly with the same regeneration buffer, also yielding an algal concentrate. The studies demonstrated that the saturation of the basic solution was not the main limiting factor in algae concentration to consider. More importantly, the technical issue involved the turgid algae paste, which was increasingly difficult to filter off of the resin as the concentration factor increased.

Commercial application: This study demonstrated that functionalized resin could be used to bind and concentrate algae out of a dilute suspension. The high binding capacity resin tested in the concentration studies, with capacity approximately 0.1 gram of algae per gram resin, was used as a specification benchmark for projecting the industrial application of binding polymer. It should be noted however that the 0.1 g algae per gram resin is based on the use of a particular size resin bead for all studies and is useful primarily for comparisons of one resin to another. This number will change with different size beads since the volume of resin grows as a function of the radius cubed whereas the surface area grows as a function of radius squared. Since these resins do not contain internal pores of a size that would let algae enter into the resin, key issue for binding is the surface area. Given the average size of the resin particles that were used for these studies, prepared by sifting the resin through sizing sieves, and by making the assumption that they are spherical, it becomes possible to obtain a surface area per gram resin and therefore, a binding capacity of 1 gram of algae per 0.2 square meter surface area.

Figure 6:
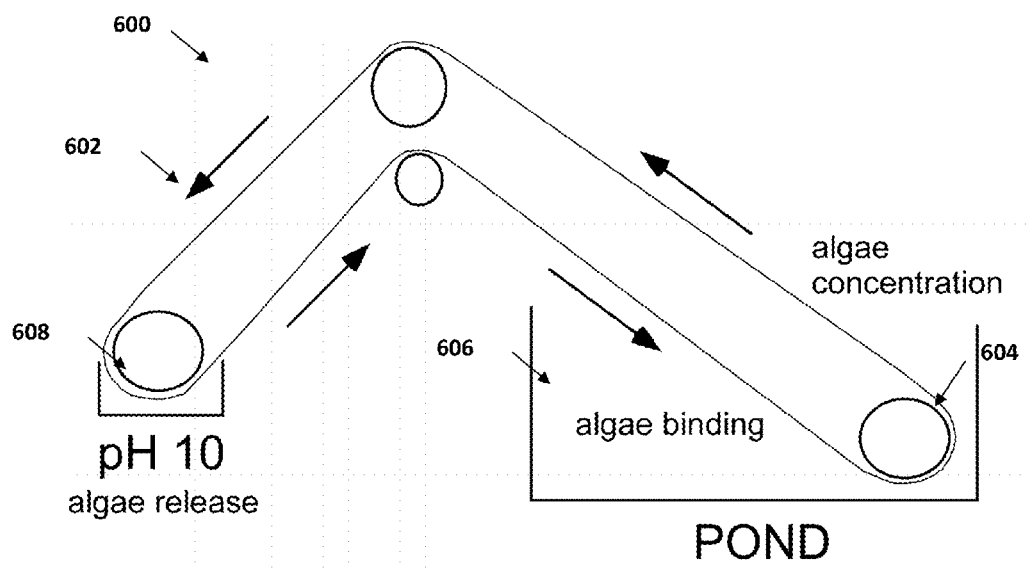
FIG. 6 is a schematic for algal harvest by reversibly-binding resins in industrial application. The resin is applied as a high surface area substrate over a rotating platform, such as a conveyor belt.

For example, the high surface area of the resin beads could be matched by a resin-coated bristle surface. A schematic 600 for such an implementation is shown in FIG. 6. A conveyor belt 602, 1 meter in depth and 7.5 meters in length, covered with bristles 604 that are 1 millimeter in diameter and 10 centimeters in length, could be turned at 1 RPM to process 1981 gallons of water and recover 3 kilogram of algae in a minute. Such a belt 602 could be placed within current raceway ponds, which already require paddles for culture circulation. To remove the algae, the belt 602 could either be physically removed and cleared, or could cycle through a separate tank for algal concentration.

While apparently similar to chemical flocculation, the polymer harvesting method offers specific advantages. First, the polymers quickly adsorb algae when the pH of the medium is below the pKa of the polymer. Flocculation by pH shift requires the substantial addition of sodium hydroxide or lime in order to induce flocculation, which can affect the integrity of the algal cells [15]. Secondly, the algae can be desorbed from the polymers, facilitating the regeneration and reuse of the resin. Flocculants are usually salts or polyelectrolytes that are not normally recovered from the material they aggregate. Thirdly, the present inventors have found that algae desorbed from the polymers are still viable and can be resuspended, while flocculation can often result in irreversible aggregates [14].

The amount of algae bound to a belt would depend on a number of factors including pond algae concentration, pond volume, belt residence time and rate of culture flow over the belt. However, even if the belt was not saturated, it should not greatly affect the final concentration of the harvest. This is because the eluting solution can be reused, or alternatively, a belt could be cycled through the solution until a maximum concentration (at least 50 g $L^{-1}$) is achieved. In terms of economy of use, it is worthwhile to compare the use of resins with pH-dependent autoflocculation, a method of harvesting that also depends on a pH change.

Both methods are, in some sense, charge neutralization methods for harvesting algae. A pH of approx. 11 is typically needed to flocculate algae efficiently [20-26] and one of the most economical ways to elevate the pH is to add lime (calcium oxide) or quicklime (calcium hydroxide or hydrated lime) to the algal suspension. Raising the pH above 10 converts magnesium salts in the media to magnesium hydroxide, which is thought to be the main flocculant [27]. It should be noted that raising the pH causes other salts such as calcium carbonate to form which coprecipitate with the algae.

Resins can be eluted using lime or calcium hydroxide as the base (data not shown) and for the DMA resin, the pH needed is similar to that required to flocculate algae (approx. 11). Furthermore, once algae are eluted with a pure calcium hydroxide solution, algae will flocculate upon standing. Thus one can draw a number of parallels between resin-based harvesting and autoflocculation using calcium hydroxide as the base. Despite these similarities, there are important differences.

With autoflocculation, supersaturated solutions are often generated to speed the flocculation and settling such that the resultant sludge contains a large amount of inorganic precipitate (mainly calcium carbonate) [28]. Thus relatively large amounts of lime are needed to maintain the pH while driving the formation of calcium carbonate. Furthermore, when used for harvesting, large volumes of water must be treated with time. In eluting resins with calcium hydroxide, only small volumes of water are needed and algae flocculate without forming an inorganic precipitate. Interestingly, elution of resin-bound algae with pure calcium hydroxide solutions runs counter to expectations since magnesium hydroxide is thought to be the active flocculant.

The resins in this study bind the algae in seawater, that is, under high salt conditions. All commercial resins tested were ineffective at binding in salt water. Given that algae can be eluted into a low salt medium, depending on how effectively saltwater is drained from the algae, some degree of desalting could be achieved. Improved desalting can be obtained for resin-bound algae by washing with fresh water prior to elution. This is one factor when considering the use of algae grown in saltwater for feedstock or fertilizer. The polymer harvesting method can be implemented in a more practical manner than chemical flocculation, while maintaining its low operating cost.

In the case where the eluting base is calcium hydroxide the eluted algae upon standing will flocculate. The flocculation further concentrates the eluted algae such that it can be collected by plate settler, filtration, or other partitioning systems. With a typical flocculation systems an alkali such as lime or quicklime is used to elevate the pH the actual flocculation is due to magnesium ions in the medium. Therefore, the water can be tested and in some cases supplemented with magnesium to achieve flocculation. Using the above-described resin-based flocculation, magnesium ions are not required to achieve flocculation. Therefore, water testing for magnesium content and supplementation is not required.

Whereas with typical flocculation excess alkali is often added to supersaturate the solution in order to increase the rate of flocculation. Furthermore, the resulting flocc becomes mixed with inorganic precipitate which must be separated from the algae. Using the above-described resin-based flocculation, elution of the algae is rapid but no inorganic salts are precipitated.

With bulk flocculation, most of the volume water containing the algal suspension can be harvested, as might be embodied in a growth pond, treated with alkali (or other flocculant) in order to initiate flocculation. With the above-described resin-based flocculation, the water from the algal suspension is separated from the algae prior to elution of algae off the resin. This water can be returned to the pond or other source and reused without being contaminated by alkali or other flocculants.

With the above-described resin-based flocculation, algae are separated from the growth medium and concentrated onto the resin. Therefore, only a small volume of material, the resin containing the bound algae need, to be treated with calcium hydroxide solution. In this case, potentially much less alkali flocculant is needed as compared to bulk flocculation. As opposed to regular flocculation, the present invention used the term "bulk autoflocculation" to refer to the situation in which raising the pH of large volumes of algal culture (such as a growth pond) in order to precipitate and harvest the algae.

The resins of the present invention can also be used for direct transesterification. Immobilized resins and the methods for making them can be found in, e.g., U.S. Patent Publication No. 2011/0083360, filed by M. Poenie, et al., on Oct. 13, 2010, relevant portions incorporated herein by reference. In the special case where the solution used to elute the algae is an alcohol such as, e.g., methanol, ethanol, propanol, etc., and a base catalyst (e.g., sodium methoxide, sodium ethoxide, sodium hydroxide or potassium hydroxide), elution of the algae is effected and upon standing, fatty acids contained in algal lipids are directly transesterified by the alcohol leading to direct formation of the corresponding fatty acid ester.

In the special case where the solution used to elute the algae includes an alcohol such as, e.g., methanol, ethanol, propanol, etc., and an acid catalyst (e.g., sulfuric acid, hydrochloric acid, phosphoric acid) is added, algae are eluted from the resin and upon standing fatty acids contained in algal lipids are directly transesterified by the alcohol to give the corresponding fatty acid ester.

The need to decrease fossil fuel dependence is an immediate technological concern. In order to compete with low-value petroleum products, algae biomass, more so than other high-value energy feedstocks, must be produced with low cost and highly efficient methods. Present invention demonstrates the application of a simple principle to harvest algae with less energy input than mechanical methods. It is an improvement over flocculation techniques in that it is reversible, nontoxic, and that the binding substrate is recoverable and reusable.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application Publication No. 2011/0083360: Immobilized Resins For Algal Oil Extraction.
U.S. Pat. No. 6,805,800: Method for Recovering Pigments from Algal Cultures.

NON-PATENT REFERENCES

1. Chisti, Y. (2007). Biodiesel from microalgae, Biotechnology Advances 25, 294-306.
2. Li, Q., Du, W., & Liu, D. (2008). Perspectives of microbial oils for biodiesel production, Applied Microbiology and Biotechnology 80, 749-756.
3. Li, Y., Horsman, M., Wu, N., Lan, C. Q., & Dubois-Calero, N. (2008). Biofuels from microalgae, Biotechnology Progress 24, 815-820.
4. Munoz, R. & Guieysse, B. (2006). Algal-bacterial processes for the treatment of hazardous contaminants: A review, Water Research 40, 2799-2815.
5. Gavrilescu, M. & Chisti, Y. (2005). Biotechnology—A sustainable alternative for chemical industry, Biotechnology Advances 23, 471-499.
6. Pyle, D. J., Garcia, R. A., & Wen, Z. (2008). Producing docosahexaenoic acid (DHA)-rich algae from biodieselderived crude glycerol: Effects of impurities on DHA production and algal biomass composition, Journal of Agricultural and Food Chemistry 56, 3933-3939.
7. Harwood, J. & Guschina, I. (2009). The versatility of algae and their lipid metabolism, Biochimie 91, 679-684.
8. Uduman, N., Qi, Y., Danquah, M. K., Forde, G. M., & Hoadley, A. (2010). Dewatering of microalgal cultures: A major bottleneck to algae-based fuels, Journal of Renewable and Sustainable Energy 2, 1-15.
9. Banerjee, A., Sharma, R., Chisti, Y., & Banerjee, U. C. (2002). *Botryococcus braunii:* A renewable source of hydrocarbons and other chemicals, Critical Reviews in Biotechnology 22, 245-279.
10. Grima, E. M., Belarbi, E. H., Fernandez, F. C. A., Medina, A. R., & Chisti, Y. (2003). Recovery of microalgal biomass and metabolites: Process options and economics, Biotechnology Advances 20, 491-515.
11. Park, J. B. K., Craggs, R. J., & Shilton, A. N. (2011). Recycling algae to improve species control and harvest efficiency from a high rate algal pond, Water Research 45, 6637-6649.

12. Hung, M. T. & Liu, J. C. (2006). Microfiltration for separation of green algae from water, Colloids and Surfaces B: Biointerfaces 51, 157-164.
13. Olaizola, M. (2003). Commercial development of microalgal biotechnology: From the test tube to the marketplace, Biomolecular Engineering 20, 459-466.
14. Wiley, P. E., Brenneman, K. J., & Jacobson, A. E. (2009). Improved algal harvesting using suspended air flotation, Water Environment Research 81, 702-708.
15. Bosma, R., Spronsen, W. A. V., Tramper, J., & Wijffels, R. H. (2003). Ultrasound, a new separation technique to harvest microalgae, Journal of Applied Phycology 15, 143-153.
16. Brown, M. R. & Bold, H. C. (1964). Comparative studies of the algal genera Tetracystis and Chlorococcum (pp. 213), Austin, Tex., USA: University of Texas Publication.
17. Jeffrey, S. W. & LeRoi, J. M. (1997). Simple procedures for growing SCOR reference microalgal cultures, France: UNESCO.
18. Jones, J., Manning, S., Montoya, M., Keller, K., & Poenie, M. (2012). Extraction of algal lipids and their analysis by HPLC and mass spectrometry, Journal of the American Oil Chemists' Society 89, 1371-1381.
19. Kara, A., Uzun, L., Besirli, N., & Denizli, A. (2004). Poly(ethylene glycol dimethacrylate-n-vinyl imidazole) beads for heavy metal removal, Journal of Hazardous Materials 106B: 93-99.
20. Ayoub, G. M., Lee, S. I., & Koopman, B. (1986). Seawater induced algal flocculation, Water Research 20, 1265-1271.
21. Dziubek, A. M. & Kowal, A. L. (1984). Effect of magnesium hydroxide on chemical treatment of secondary effluent under alkaline conditions, Proceedings of the Water Reuse Symposium III (pp. 1428-1436), San Diego: AWWA Research Foundation.
22. Dziubek, A. M. & Kowal, A. L. (1989). High-pH coagulation-adsorption: A new technology for water treatment and reuse, Water Science and Technology 21, 511-517.
23. Elmaleh, S., Yahi, H., & Coma, J. (1996). Suspended solids abatement by pH increase—Upgrading of an oxidantion pond effluent, Water Research 30, 2357-2362.
24. Lavoie, A. & Noue, J. D. L. (1986). Harvesting of Scenedesmus obliquus in wastewaters: Auto- or bioflocculation? Biotechnology and Bioengineering 30, 852-859.
25. Shin, H. S. & Lee, S. M. (1997). Removal of nutrients in wastewater by using magnesium salts, Environmental Technology 19, 283-290.
26. Yahi, H., Elmaleh, S., & Coma, J. (1994). Algal flocculation-sedimentation by pH increase in a continuous reactor, Water Science and Technology 30, 259-267.
27. Folkman, Y. & Wachs, A. M. (1973). Removal of algae from stabilization pond effluents by lime treatment, Water Research 7, 419-435.
28. Shelef, G., Sukenik, A., & Green, M. (1984). Microalgae harvesting and processing: A literature review. Springfield: National Technical Information Service.
29. Schlesinger, A., Eisenstadt, D., Hilla, A., Carmely, H., Einbinder, S., & Gressel, J. (2012). Inexpensive non-toxic flocculation of microalgae contradicts theories: Overcoming a major hurdle to bulk algal.

What is claimed is:

1. A method for harvesting or separating one or more biological cells from an aqueous feed, a stream, a suspension, or any combinations thereof comprising the steps of:
   (a) providing the aqueous feed, the stream, or the suspension comprising the one or more biological cells in a tank or a vessel;
   (b) providing one or more ion-exchange resins, wherein the ion-exchange resin is an anion-exchange resin, wherein the anion-exchange resin may be packed in a column, attached to a substrate, be in a solution, or any combinations thereof;
   (c) contacting the anion-exchange resin with the aqueous feed, the stream, or the suspension comprising the one or more biological cells;
   (d) binding the one or more biological cells to the anion-exchange resin, wherein the binding is done by maintaining a specific pH;
   (e) releasing or eluting the bound one or more biological cells by changing the pH by addition of an acid, a base, or one or more chemicals, wherein the change in the pH involves an increase or a decrease in the pH, wherein the release or elution of the biological cells is accomplished in a pH range of 8-13; and
   (f) collecting the released one or more biological cells to obtain a concentrated slurry of the one or more biological cells.

2. The method of claim 1, wherein the one or more biological cells comprise algal cells.

3. The method of claim 2, wherein the one or more algal cells comprise Chrysophyceae.

4. The method of claim 3, wherein the biological cells comprise the microalgal genera Chlorella.

5. The method of claim 1, wherein the anion-exchange resins comprise a cross-linked polymer backbone with one or more functional groups comprising ammonium salts, tertiary amines, secondary amines, primary amines, organometallic complexes, aromatic amines, amidinium, or guanidine groups, a charged species, or any combinations thereof.

6. The method of claim 5, wherein the polymer backbone is a selected from the group consisting of styrene, styrene-divinyl benzene, polystyrene, formophenolic, acrylic-divinyl benzene, methacryl-divinyl benzene, functionalized styrene monomers, functionalized acrylic monomers, functionalized methacrylic monomers, acrylamides, methacrylamides, epoxy and acrylic monomers, polypropylene, or functionalized polyvinyl chloride polymers.

7. The method of claim 5, wherein the one or more functional groups comprise triethylene tetramine, nitrate, piperazine, diethylenetetramine, diisopropyl ethylamine, aniline, dimethylaminoethyl methacrylate (DMA), vinyl 2-imidazole, vinyl 4-imidazole (IM), hydroxyethyl methacrylate (HEMA), di(ethylene glycol) vinyl ether (DEG), or any combinations thereof.

8. The method of claim 6, wherein the polymer backbone is a methacrylate or a divinyl benzene and the functional group is selected from the group consisting of DEG, DMA, IM, PYR, or any combinations thereof.

9. The method of claim 1, wherein the method further comprises the steps of:
   (g) processing the concentrated slurry comprising the one or more biological cells in a processing unit to yield an oil or biodiesel; and
   (h) reusing the anion-exchange resin to harvest or separate a subsequent batch of the one or more biological cells from the aqueous feed, the stream, the suspension, or any combinations thereof.

10. The method of claim 9, wherein the processing unit comprises:
   one or more lysing units to electromechanically lyse the one or more biological cells by an application of an electromagnetic field, wherein the lysis results in a release of one or more cellular components comprising oils, neutral lipids, proteins, triglycerides, sugars or combinations and modifications thereof from the biological cells;
   one or more separations unit to separate the released oils and lipids from the medium resulting in a generation of a residual biomass; and one or more optional pumping equipment, heat exchangers, distilling equipment, reboilers, condensors, and combinations and modifications thereof.

11. The method of claim 1, wherein a pKa value of the one or more anion-exchange resins ranges from 5.5-12.

12. The method of claim 1, wherein the method results in a 50-70 fold concentration of the one or more biological cells.

13. The method of claim 1, further comprising the step of eluting the biological cells in the presence of a base, wherein the biological cells spontaneously flocculate after elution and upon standing.

14. The method of claim 1, further comprising the step of eluting the biological cells in the presence of a base selected from at least one of calcium hydroxide or magnesium hydroxide, and wherein the algae spontaneously flocculate after elution and upon standing and are collected using a plate settler, a filtration system, or a partitioning system.

15. The method of claim 1, wherein the biological cell flocculation occurs solely in the presence of the resin.

16. The method of claim 1, wherein the biological cell flocculation occurs in the presence of the resin and the biological cells are separated from the water prior to elution of the biological cells from the resin.

17. The method of claim 1, further comprising the step of eluting the biological cells from the resin in the presence of an alcohol and a base catalyst, wherein fatty acids obtained from the biological cells are directly transesterified by the alcohol leading to direct formation of the corresponding fatty acid ester.

18. The method of claim 1, further comprising the step of eluting the biological cells from the resin in the presence of an alcohol selected from at least one of methanol, ethanol, propanol, butanol, or hexanol, and a base catalyst selected from at least one of sodium methoxide, sodium ethoxide, sodium hydroxide or potassium hydroxide, wherein fatty acids obtained from the biological cells are directly transesterified by the alcohol leading to direct formation of the corresponding fatty acid ester.

19. The method of claim 1, further comprising the step of eluting the biological cells from the resin in the presence of an alcohol selected from at least one of methanol, ethanol, propanol, butanol, or hexanol, in the presence of an acid catalyst, wherein fatty acids obtained from the biological cells are directly transesterified by the alcohol leading to direct formation of the corresponding fatty acid ester.

20. The method of claim 1, wherein the anion exchange resin is

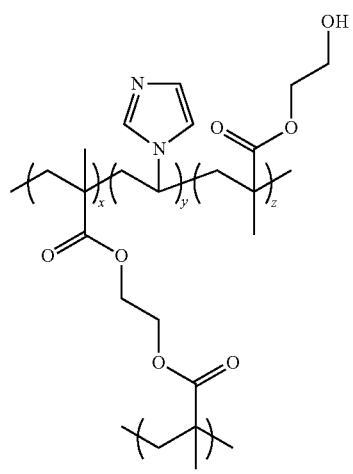

wherein x=60, y is a number ranging from 10-30, and z is a number ranging from 10-30.

21. A method for harvesting or separating one or more algal cells from an aqueous feed, slurry, or suspension comprising the steps of:

(a) providing the aqueous feed, the slurry, or the suspension comprising the one or more algal cells;

(b) saturating an anion-exchange resin in a column or a container with the algal suspension or slurry;

(c) binding the one or more algal cells to the anion-exchange resin, wherein the binding is done by maintaining a specific pH;

(d) flowing an eluent through the algae saturated column to release or elute the bound algae off the column by a change in the pH, wherein the change in the pH is achieved by addition of an acid, a base, or one or more chemicals, wherein the release or elution of the bound biological cells is accomplished in a pH range of 8-13; and (e) collecting the released one or more algal cells to obtain a concentrated slurry of the one or more biological cells.

22. The method of claim 21, further comprising the steps of:

(f) removing any excess water of liquids from the column or the container by applying a gas pressure, applying a vacuum, air drying the column or the container or using a combination of other drying techniques;

(g) processing the concentrated slurry comprising the one or more algal cells in a processing unit to yield an oil or biodiesel; and (h) reusing the anion-exchange resin to harvest or separate a subsequent batch of the one or more algal cells from the aqueous feed, the slurry, or the suspension.

23. The method of claim 21, wherein the one or more algal cells comprise microalgae selected Chrysophyceae.

24. The method of claim 23, wherein the microalgal genera is *Chlorella*.

25. The method of claim 21, wherein the anion-exchange resins comprise a cross-linked polymer backbone with one or more functional groups comprising ammonium salts, tertiary amines, secondary amines, primary amines, organometallic complexes, aromatic amines, amidinium, or guanidine groups, any charged species, or any combinations thereof.

26. The method of claim 21, wherein the polymer backbone is a selected from the group consisting of styrene, styrene-divinyl benzene, polystyrene, formophenolic, acrylic-divinyl benzene, methacryl-divinyl benzene, functionalized styrene monomers, functionalized acrylic monomers, functionalized methacrylic monomers, acrylamides, methacrylamides, epoxy and acrylic monomers, polypropylene, or functionalized polyvinyl chloride polymers.

27. The method of claim 21, wherein the one or more functional groups comprise triethylene tetramine, nitrate, piperazine, diethylenetetramine, didisopropyl ethylamine, aniline, dimethylaminoethyl methacrylate (DMA), vinyl 2-imidazole, vinyl 4-imidazole (IM), hydroxyethyl methacrylate (HEMA), or any combinations thereof.

28. The method of claim 26, wherein the polymer backbone is a methacrylate or a divinyl benzene and the functional group is selected from the group consisting of DMA, IM, PYR, or any combinations thereof.

29. The method of claim 21, wherein the anion-exchange resin is

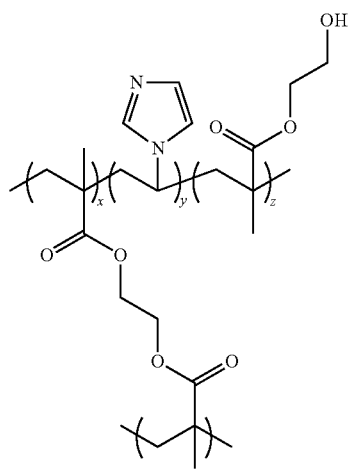

wherein x=60, y is a number ranging from 10-30, and z is a number ranging from 10-30.

30. The method of claim 21, wherein the release or elution of the bound one or more biological cells is accomplished in a pH range of 8-13.

31. The method of claim 21, wherein a pKa value of the one or more anion-exchange resins ranges from 5.5-12.

32. The method of claim 21, wherein the method results in a 50-70 fold concentration of the one or more biological cells.

33. The method of claim 21, further comprising the step of eluting the biological cells in the presence of a base, wherein the biological cells spontaneously flocculate after elution and upon standing.

34. The method of claim 21, further comprising the step of eluting the biological cells in the presence of a base selected from at least one of calcium hydroxide or magnesium hydroxide, and wherein the algae spontaneously flocculate after elution and upon standing and are collected using a plate settler, a filtration system, or a partitioning system.

35. The method of claim 21, wherein biological cell flocculation occurs concomitant with or upon release of the biological cell concentrated by the resin.

36. The method of claim 21, wherein biological cell flocculation occurs in the presence of the resin and the biological cells are separated from the water prior to elution of the biological cells from the resin.

37. The method of claim 21, further comprising the step of eluting the biological cells from the resin in the presence of an alcohol and a base catalyst, wherein fatty acids obtained from the biological cells are directly transesterified by the alcohol leading to direct formation of the corresponding fatty acid ester.

38. The method of claim 21, further comprising the step of eluting the biological cells from the resin in the presence of an alcohol selected from at least one of methanol, ethanol, propanol, butanol, or hexanol, and a base catalyst selected from at least one of sodium methoxide, sodium ethoxide, sodium hydroxide or potassium hydroxide, wherein fatty acids obtained from the biological cells are directly transesterified by the alcohol leading to direct formation of the corresponding fatty acid ester.

39. The method of claim 21, further comprising the step of eluting the biological cells from the resin in the presence of an alcohol selected from at least one of methanol, ethanol, propanol, butanol, or hexanol, in the presence of an acid catalyst, wherein fatty acids obtained from the biological cells are directly transesterified by the alcohol leading to direct formation of the corresponding fatty acid ester.

40. A method of concentrating an aqueous suspension of *Chlorella*, comprising the steps of:
(a) providing the dilute aqueous suspension comprising the *Chlorella*;
(b) saturating an anion-exchange resin in a column or a container with the dilute suspension, wherein the anion-exchange resin has a structure given by:

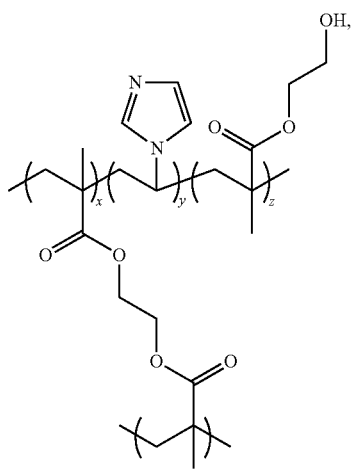

wherein x=60, y=30, and z=10;
(c) binding the one or more *Chlorella* cells to the anion-exchange resin, wherein the binding is done by maintaining a specific pH;
(d) flowing an eluent through the *Chlorella* saturated column to release or elute the bound *Chlorella* off the column by a change in the pH, wherein the change in the pH is achieved by addition of an acid, a base, or one or more chemicals, wherein the release or elution of the bound biological cells is accomplished in a pH range of 8-13; and
(e) collecting the released *Chlorella* cells to obtain a concentrated slurry.

41. The method of claim 40, further comprising the steps of:
(f) processing the concentrated slurry or suspension comprising the *Chlorella* cells in a processing unit to yield an oil or biodiesel; and
(g) reusing the anion-exchange resin to harvest or separate a subsequent batch of the one or more *Chlorella* cells from the slurry, or the suspension.

* * * * *